US010064548B2

(12) United States Patent
Maddess et al.

(10) Patent No.: US 10,064,548 B2
(45) Date of Patent: Sep. 4, 2018

(54) METHOD AND APPARATUS FOR SENSORY FIELD ASSESSMENT

(75) Inventors: Teddy Lee Maddess, Lyneham (AU); Andrew Charles James, Campbell (AU)

(73) Assignee: The Australian National University, Acton, Canberra (AU)

( * ) Notice: Subject to any disclaimer, the term of this patent is extended or adjusted under 35 U.S.C. 154(b) by 689 days.

(21) Appl. No.: 12/741,762

(22) PCT Filed: Nov. 7, 2008

(86) PCT No.: PCT/AU2008/001663
§ 371 (c)(1),
(2), (4) Date: May 6, 2010

(87) PCT Pub. No.: WO2009/059380
PCT Pub. Date: May 14, 2009

(65) Prior Publication Data
US 2010/0249532 A1 Sep. 30, 2010

(30) Foreign Application Priority Data

Nov. 9, 2007 (AU) .............................. 2007906174

(51) Int. Cl.
*A61B 3/00* (2006.01)
*A61B 5/00* (2006.01)
(Continued)

(52) U.S. Cl.
CPC .......... *A61B 3/024* (2013.01); *A61B 5/04842* (2013.01)

(58) Field of Classification Search
CPC ....... A61B 5/0484; A61B 5/16; A61B 5/6814; A61B 5/04842; A61B 5/0496
(Continued)

(56) References Cited

U.S. PATENT DOCUMENTS 4,421,392 A * 12/1983 Pitts Crick et al. .......... 351/224
4,493,539 A *  1/1985 Cannon, Jr. .................. 600/558
(Continued)

FOREIGN PATENT DOCUMENTS

JP   2003-515375    5/2003
JP   2004-008360    1/2004
(Continued)

OTHER PUBLICATIONS

Australian Examination First Report dated Dec. 11, 2012 on Australian Patent Application No. 2008324705.
(Continued)

*Primary Examiner* — Sean Dougherty
*Assistant Examiner* — Patrick Fernandes
(74) *Attorney, Agent, or Firm* — Wood, Phillips, Katz, Clark & Mortimer

(57) ABSTRACT

A method for assessing the function of at least one sensory field of a subject, and apparatus and systems for carrying out the method, the method comprising: using a display, presenting stimuli to selected locations of the sensory field, the selected locations being centered at points on a sampling grid spanning a portion of the sensory field, wherein the individual stimuli if presented simultaneously at the sampling grid points would overlap in the space defined by the sensory dimensions of the field; using a sensor, detecting responses in the subject's sensory field evoked by the stimuli; and processing the detected responses to relate them to the function of the subject's sensory field at the selected locations.

32 Claims, 21 Drawing Sheets

(51) Int. Cl.
*A61B 3/024* (2006.01)
*A61B 5/0484* (2006.01)

(58) Field of Classification Search
USPC .................... 351/224, 246; 600/300, 558
See application file for complete search history.

(56) References Cited

U.S. PATENT DOCUMENTS

| | | | | |
|---|---|---|---|---|
| 4,846,567 | A * | 7/1989 | Sutter | 351/224 |
| 5,233,373 | A * | 8/1993 | Peters | A61B 3/12 351/211 |
| 5,295,492 | A * | 3/1994 | Sellers | 600/585 |
| 5,295,495 | A | 3/1994 | Maddess | |
| 5,382,987 | A * | 1/1995 | Sperling | 600/558 |
| 5,539,482 | A * | 7/1996 | James et al. | 351/246 |
| 5,565,949 | A * | 10/1996 | Kasha, Jr. | 351/224 |
| 5,579,161 | A * | 11/1996 | Sekiguchi | G02B 27/0101 359/559 |
| 5,740,284 | A * | 4/1998 | Wober | G06F 17/147 348/E9.01 |
| 6,254,536 | B1 * | 7/2001 | DeVito | 600/300 |
| 6,315,414 | B1 * | 11/2001 | Maddess et al. | 600/558 |
| 6,406,437 | B1 * | 6/2002 | Zur et al. | 600/558 |
| 6,475,162 | B1 * | 11/2002 | Hu | 600/558 |
| 6,688,746 | B2 * | 2/2004 | Malov | 600/558 |
| 7,004,912 | B2 * | 2/2006 | Polat | 600/558 |
| 7,006,863 | B2 * | 2/2006 | Maddess et al. | 600/544 |
| 7,469,159 | B2 * | 12/2008 | DeYoe et al. | 600/411 |
| 7,474,775 | B2 * | 1/2009 | Abramoff et al. | 600/558 |
| 7,486,988 | B2 * | 2/2009 | Goodall et al. | 600/546 |
| 7,488,294 | B2 * | 2/2009 | Torch | 600/558 |
| 2002/0049389 | A1 * | 4/2002 | Abreu | 600/558 |
| 2003/0081176 | A1 | 5/2003 | Stewart | |
| 2003/0158497 | A1 * | 8/2003 | Graham et al. | 600/558 |
| 2003/0163060 | A1 * | 8/2003 | Maddess et al. | 600/544 |
| 2004/0071363 | A1 * | 4/2004 | Kouri et al. | 382/276 |
| 2004/0263780 | A1 * | 12/2004 | Hu et al. | 351/205 |
| 2006/0184062 | A1 * | 8/2006 | Greenberg et al. | 600/558 |
| 2007/0188710 | A1 | 8/2007 | Hetling et al. | |
| 2007/0287932 | A1 * | 12/2007 | Huang et al. | 600/558 |

FOREIGN PATENT DOCUMENTS

| | | |
|---|---|---|
| WO | WO 99/58046 A1 | 11/1999 |
| WO | WO 01/78586 A1 | 10/2001 |
| WO | WO 06/23964 A2 | 3/2006 |

OTHER PUBLICATIONS

Extended European Search Report (ESSR) dated Oct. 24, 2013 on European Patent Application No. 08847577.7.
Bearse et al, "Imaging localized retinal dysfunction with the multifocal electroretinogram", Journal of the Optical Society of America, Optics and Image Science, Optical Society of America, US, vol. 13, Jan. 1, 1996, pp. 634-610, XP007909157.
Japanese Office Action dated Feb. 19, 2014 on Japanese Patent Application No. 2010-532381.
English translation of entire Japanese Office Action dated Feb. 19, 2014 on Japanese Patent Application No. 2010-532381.
Marks, Lawrence E., "On colored-hearing synesthesia: Cross-modal translations of sensory dimensions," Psychological Bulletin, vol. 82(3), May 1975, 303-331.
English summary of Japanese Office Action dated Feb. 19, 2014 on Japanese Patent Application No. 2010-532381.
Davis, Stephen F. (editor), Handbook of Research Methods in Experimental Psychology, Blackwell Publishing Ltd, ISBN 0-631-22649-4, 2008, p. 462.
Roeckelein, J.E., Elsevier's Dictionary of Psychological Theories, Elsevier B.V., 1st Edition, ISBN 0-444-51750-2, 2006, p. 624.
Canadian Office Action dated Mar. 6, 2015.

* cited by examiner

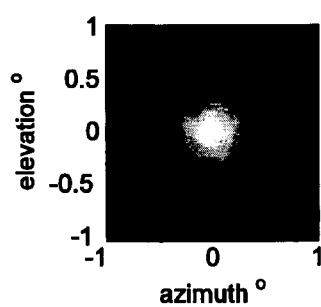
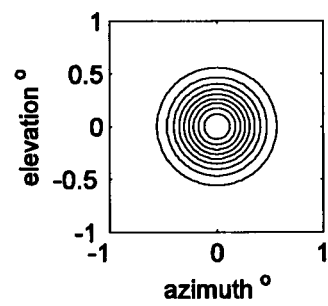
Figure 5A
Figure 5B
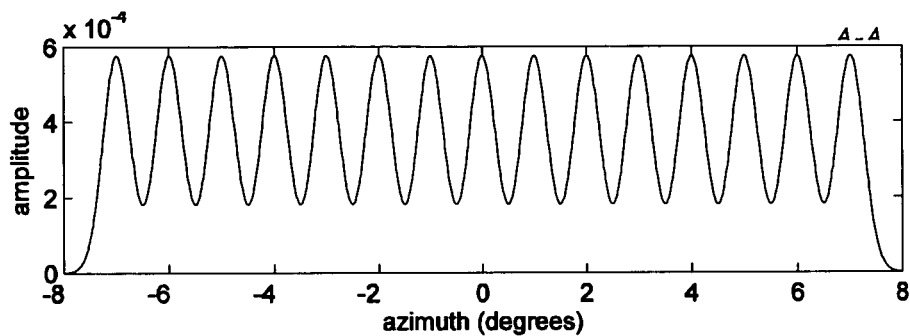
Figure 5C
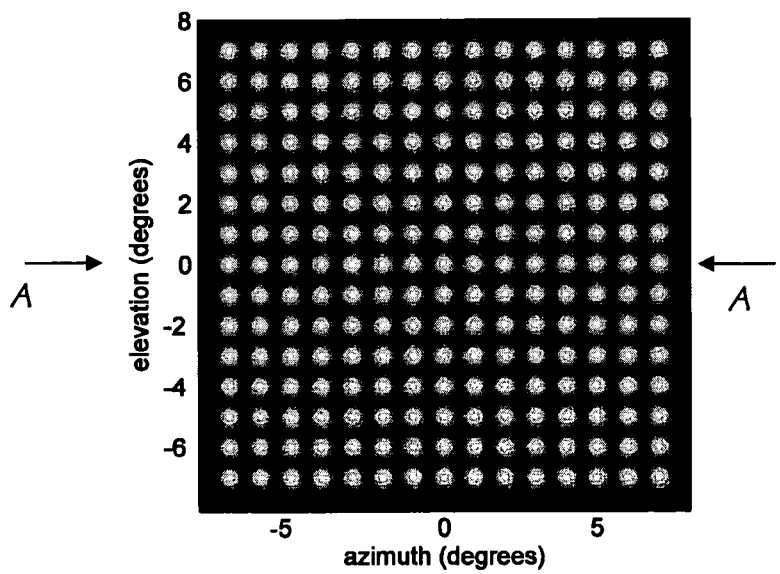
Figure 5D

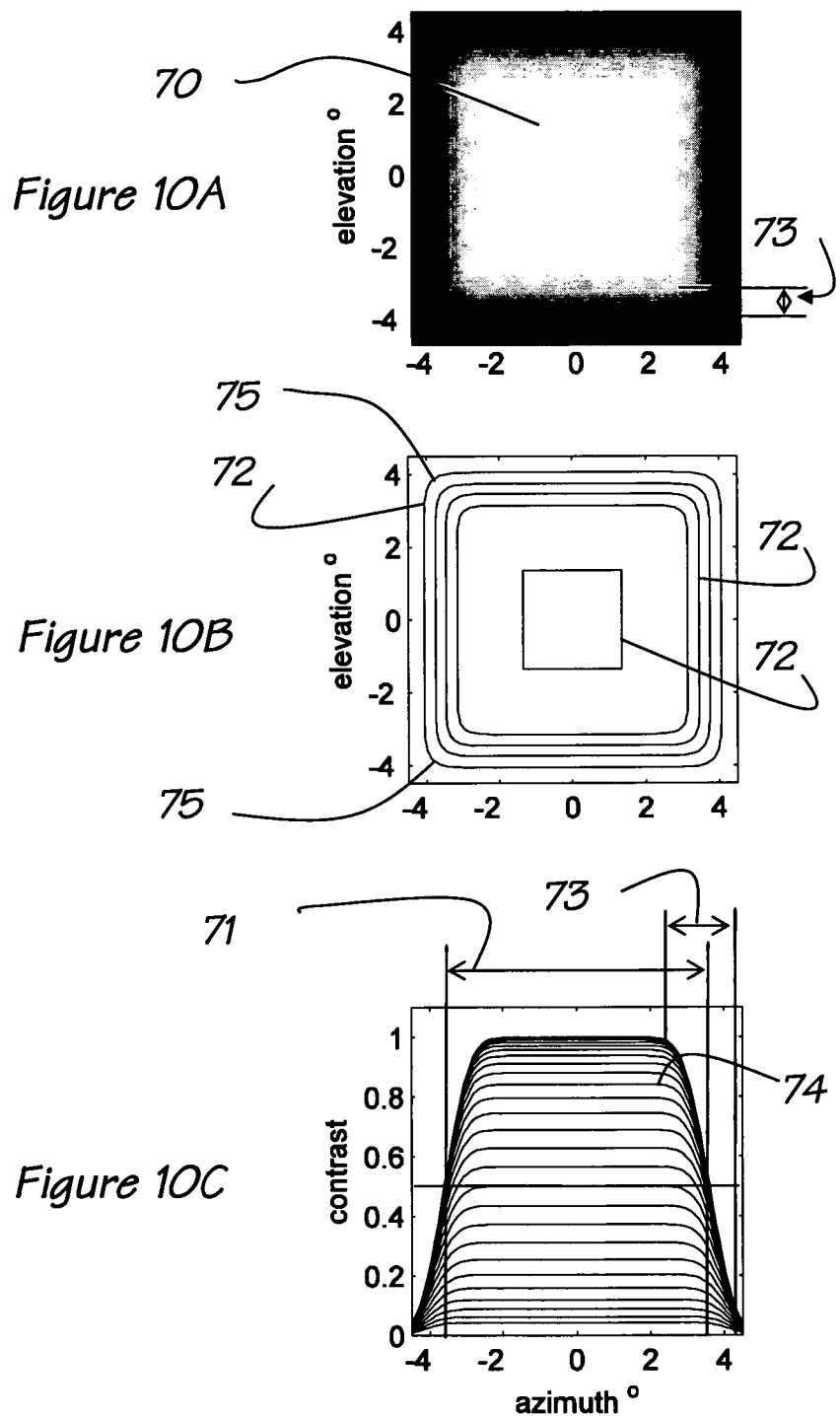

30-2 stimulus ensembles 30-2 stimulus ensembles respecting meridians

Overlapping FPT N-30 Stimulus Ensemble

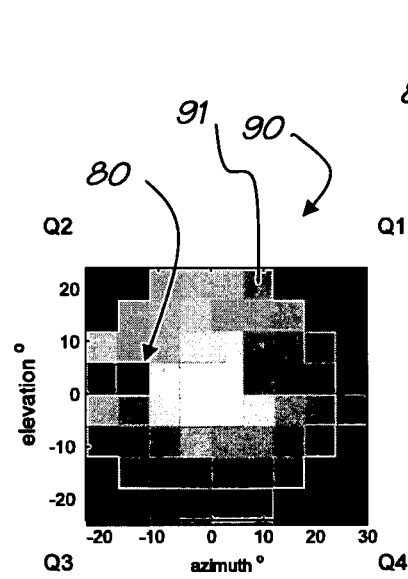
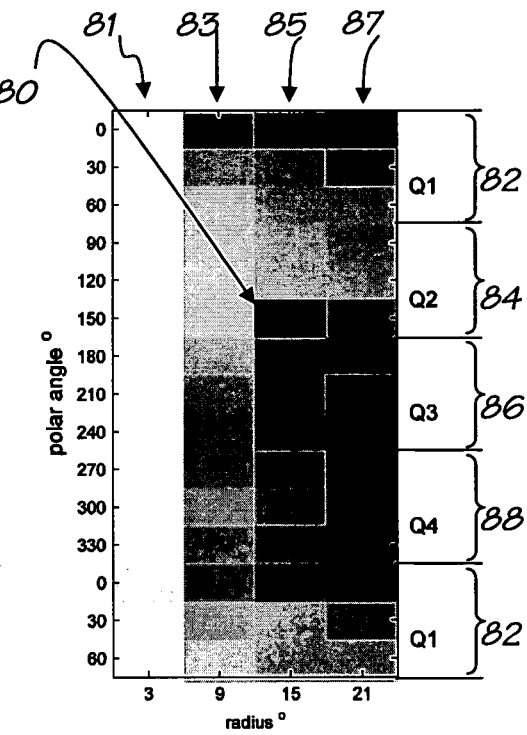
Figure 15A   Figure 15B
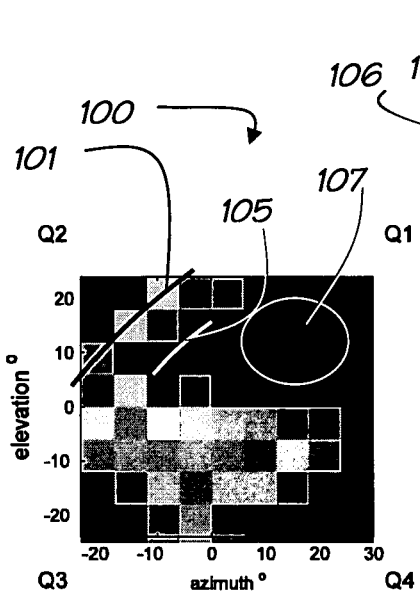
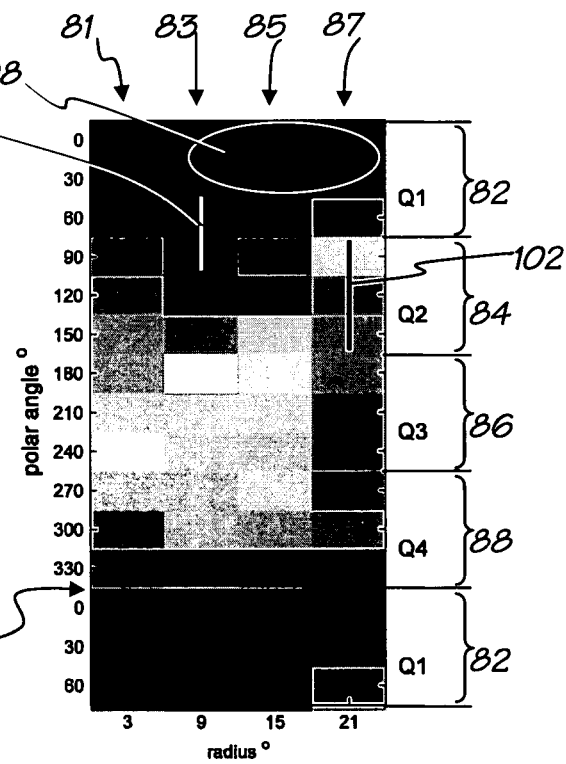
Figure 16A   Figure 16B

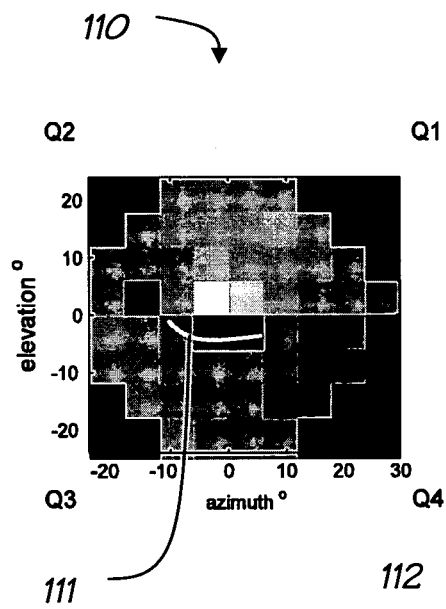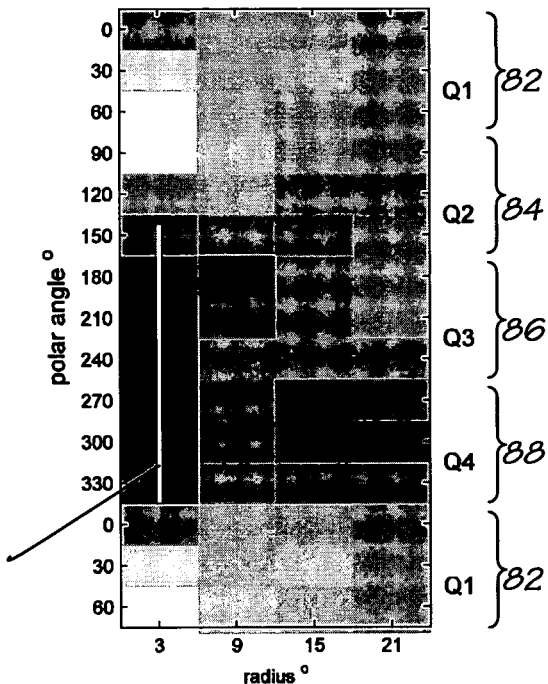
Figure 17A        Figure 17B
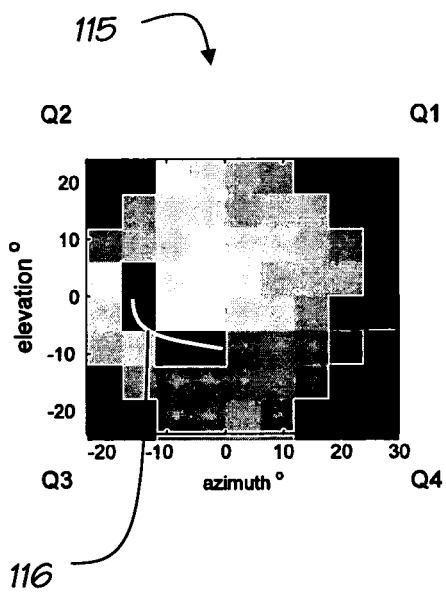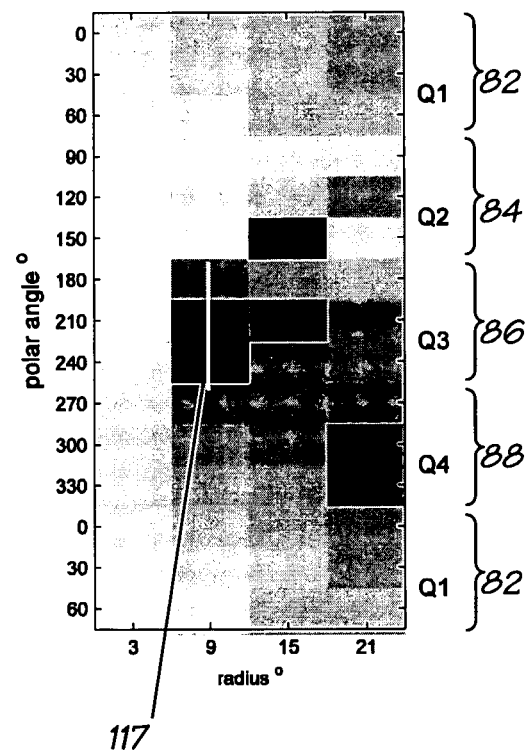
Figure 18A        Figure 18B Overlapping Polar Stimulus Ensemble

Median Filters

Linear Filters

METHOD AND APPARATUS FOR SENSORY FIELD ASSESSMENT

TECHNICAL FIELD

The present invention relates to assessment of the function of the nervous system and in particular to the assessment of sensory fields of multiple sensory dimensions, and most particularly the two dimensional visual sensory field.

The invention has been developed primarily for use as a method and apparatus for improved assessment and quantification of the sensory fields field of human and animal subjects, particularly the visual fields of eyes as and will be described hereinafter with reference to this application. However, it will be appreciated that the invention is not limited to this particular field of use. These sensory fields are defined in terms of measures of sensory neural ability at a collection of points in the sensory field. The invention herein described provides methods and apparatus for more accurately determining variations in these sensory fields which, in turn may be related to disease processes or natural processes including growth, aging, eyelids, spectacle frame position, or skull shape, all of which can either change the sensitivity of the fields or the physical limits of the extent of the fields.

BACKGROUND OF THE INVENTION

Any discussion of the background art throughout the specification should in no way be considered as an admission that such background art is prior art, nor that such background art is widely known or forms part of the common general knowledge in the field.

The visual field of humans is commonly assessed by static perimetry. In static perimetry it is common practice to sequentially present small spots of light at each of a preset collection of points distributed across the visual field. Following each presentation of a test spot subjects indicate whether or not they have seen the test light just presented while they maintain their gaze on a fixation target. Typically subjects will give a behavioural response, such as pressing a button, to indicate that they have seen the spot. Particular parts of the visual field can have their own visual ability. The goal of perimetry is thus to assess the visual ability of each part of the visual field.

Visual ability is often characterized by sensitivity or reliability for seeing the spot stimuli. Thus for these behavioural based forms of perimetry two basic methods exist: supra-threshold and threshold perimetry. In supra-threshold perimetry several presentations are made at each of a set of preset locations in the visual field, and then the frequency of correct responses is used to estimate visual ability. In threshold perimetry the intensity or contrast of the test stimuli is varied according to a strategy to determine the fraction of the starting stimulus strength, i.e. a threshold, at which a criterion minimum frequency of seeing is obtained. Other stimulus variables that are manipulated in order to determine local visual sensitivity are the number of small objects presented to a given test region, or the size of the test stimuli presented. Visual sensitivity is thus equated with the inverse of the threshold stimulus fraction, small threshold values thus equating to large sensitivities.

An alternative and more objective method of mapping the visual field is to use so-called multifocal methods. In these methods one uses an ensemble of stimuli each presented to a different visual field location. The appearance or non-appearance of stimuli at each location is modulated by temporal sequences that are mutually statistically independent. Ideally this statistical independence should be complete, i.e. the modulation sequences should be orthogonal. A variety of patents related to particular orthogonal (U.S. Pat. No. 5,539,482 to Maddess & James, the disclosure of which are wholly incorporated herein by cross-reference) and near orthogonal sequences including (U.S. Pat. No. 4,846,567 to Sutter), exist but recent analysis methods permit more general stimuli to be used as described in U.S. Pat. Nos. 6,315,414; 7,006,863 and International Patent Publication No. WO 2005/051193, all to Maddess & James, the disclosures of which are wholly incorporated herein by cross-reference.

The general idea of multifocal methods is that the temporal statistical independence of the stimuli permits many sequences to be presented concurrently, and for the estimated response to presentations at each location to be recovered from recordings of neural activity of the visual nervous system. The neural responses to the stimuli can be recorded by electrical or magnetic sensor or detectors, changes to the absorption, scattering or polarization infrared light or other electromagnetic radiation, functional magnetic resonance imaging, or responses of the pupils.

Static perimetry arose from dynamic perimetry in which handheld stimuli of fixed sizes were moved from the peripheral visual field towards its centre, i.e. the point of gaze fixation. In dynamic perimetry the subject indicates at what point the test stimulus is seen along its centrally directed trajectory. The minimum sized stimulus that can be seen at a given distance from the centre of the visual field is taken as an indication of visual sensitivity. The most influential dynamic perimetry system is the 1945 Goldmann system. The Goldmann system defined a set of standard stimulus spot sizes. These have subsequently been quite universally adopted as the standard stimulus sizes for most static perimeters. Static perimeters offer automated standardization of the test procedure and mainly for that reason have largely supplanted dynamic perimetry. The word static in the name derives from the test stimuli being flashed at fixed points, these points typically being arranged in a regular sampling grid. The two commonest systems for conducting static perimetry tests are various versions of the Humphrey Field Analyser (HFA) produced by Carl Zeiss Meditec, and the various Octopus Perimeters produced by Haag-Streit AG. As an indication of the influence of these devices perimeters manufactured by other companies often claim substantial equivalence with the HFA to obtain approval by the United States Food and Drug Administration.

The standard test stimulus for many static perimeters is the Goldman size III. Occasionally the larger size V stimulus is used. Test grids employed in the most common static perimetry tests cover the central 24 to 30 degrees of the visual field. The sample grid is a square grid of points, with a typical separation of 6 degrees and 50 or more of these test locations are examined. The axes of the test grids are oriented horizontally and vertically. Some static perimeters permit the test grid to be uniformly shrunk or expanded to have a separation of 2 degrees. The HFA is frequently regarded as the gold standard and has been the largest selling perimeter. The most commonly used HFA test, which others emulate, is the HFA 24-2 test pattern with its 6 degree separation of test points. The Goldmann size III spot has a diameter of 0.431 degrees. The standard HFA 24-2 test grid has 54 test locations so the test spots collectively cover 7.84 $deg^2$. The area of the visual field spanned by the 24-2 pattern is 1368 $deg^2$ (i.e. the grid of points in the 24-2 pattern defines 38 squares, each 6 degrees on a side hence 38*36 deg2=1368 deg$^2$). Thus the test spots collectively sample only 0.573% of the tested visual field area. Most other perimeters have similarly low coverage of the visual field. Evidently there is considerable scope to miss significant details of the visual field. This problem is commonly referred to as undersampling. Undersampling was less of a problem when the same spot sizes were used in dynamic perimetry but where the spot was swept with an unbroken motion along paths across the visual field, there was the potential that no part of the retina was missed.

If two-dimensional sampling techniques are considered, it is clear that the consequences of undersampling are worse than simply missing valuable or important information. Rather, when the sampling grid is too coarse to capture rapid changes in sensitivity across the visual field, the HFA sampling scheme is capable of distorting the appearance of the measured visual field. This occurs when the sampling grid is too coarse to capture rapid changes in sensitivity across the visual field. More specifically, any sampling grid with a regular spacing of s degrees defines a critical sampling frequency, $S_c$, which is the highest spatial frequency the sampling array can reliably represent. $S_c$ is sometimes called the Nyquist sampling frequency. For the 6 degree sampling spacing common in static perimeters $S_c$ varies between 1/12 cycles per degrees (cpd) horizontally and vertically, to 1/(12*√2) diagonally. Thus, if the visual field has spatial modulations that vary faster than $S_c$ cycles per degrees (cpd) that these will appear in the sampled field as lower spatial frequencies through a process called aliasing. Moiré patterns and the 'jazzing' effects of thinly striped objects viewed on television are common examples of artifacts caused by aliasing.

These distortions of the sampled image occur because the spatial frequencies that are higher than $S_c$, $S>S_c$, that occur between than $NS_c$ and $(N+1)S_c$ (where the N are the odd integers starting with 1) will appear to have frequencies $S_c$-rem($S,S_c$), and at frequencies rem($S,S_c$) for even N and beginning with 2, rem being the remainder function. More simply frequencies in the visual field above $S_c$ appear as some frequency lower than $S_c$ at various phases and orientations producing spatially distorting effects. Because these higher frequencies masquerade as low frequencies these incorrectly measured frequencies are sometimes referred to as aliases, and the process as aliasing.

Anti-aliasing filters are very common in the front-end electronics of digitizing systems. That is, higher frequencies that the sampling frequency can reconstruct are removed before sampling, however, such temporal filters do not assist in the removal of any spatial aliasing. Therefore, there is a need for an improved assessment method which can overcome the effects of spatial aliasing in the test stimuli.

SUMMARY OF THE INVENTION

According to a first aspect, there is provided a method for assessing the function of at least one sensory field of a subject. The method may comprise presenting stimuli to selected locations of the at least one sensory field. The selected locations may be centred at points on a sampling grid spanning a portion of the at least one sensory field. The individual stimuli, if presented simultaneously at the sampling grid points, may be configured such that they would overlap in the space defined by the sensory dimensions of the field. The stimuli presented to the subject's visual field may evoke associated response(s). The individual stimuli may be large and smooth sided such that they do not individually represent spatial frequencies higher than those that can be represented by the sampling grid.

The method may further comprise the step of detecting the responses in the subject's sensory field(s) using a sensor. The method may further comprise the step of processing the detected responses. The step of processing the detected response may be to relate the detected responses to the function of the subject's sensory field(s) at the selected locations.

In an arrangement of the first aspect, there is provided a method for assessing the function of at least one sensory field of a subject, the method comprising:

presenting stimuli to selected locations of the sensory field, the selected locations being centred at points on a sampling grid spanning a portion of the at least one sensory field, wherein the individual stimuli if presented simultaneously at the sampling grid points would overlap in the space defined by the sensory dimensions of the at least one field;

using a sensor, detecting responses in the subject's sensory field evoked by the stimuli; and processing the detected responses to relate them to the function of the subject's sensory field at the selected locations.

The stimuli may be configured such that, if presented simultaneously, individual stimuli may be sufficiently overlapping and smooth sided such that spatial aliasing of the stimuli on the sampling grid is minimised. The individual stimuli may be sufficiently large and smooth sided such that they do not individually represent spatial frequencies higher than those that can be represented by the sampling grid. That is, the stimuli may transmit little to no spatial frequencies that the sampling grid cannot represent accurately. The stimuli may alternatively or concurrently be configured such that, if presented simultaneously, individual stimuli may be sufficiently overlapping such that they transmit little to no spatial frequencies above the critical sampling frequency of the sampling grid, referred to as the Nyquist rate and defined by the geometry of the sampling grid. The profiles of the individual stimuli (particularly the edges and/or corners of the profile) may be smoothly varying. The smoothly varying profiles of the individual stimuli may be sufficiently smooth such that they comprise only low spatial frequency Fourier components. The individual stimuli may be blurred. The profiles of the stimuli may be smoothly varying such that the individual stimuli contain only spatial frequencies that are less than or equal to the highest spatial frequency that can be represented by the sampling grid defined by the points of the sampling grid. The sufficiently smooth or blurred individual stimuli have the significant advantage that the subject may not be well refracted (that is, may have incorrect, insufficient or even no refractive correction) without significantly affecting the results of the assessment of the subject's visual field.

The sensory field may have a horizontal meridional axis and a vertical meridional axis, and the stimuli may be adapted such that individual stimuli do not overlap with either the vertical or horizontal meridional axes of the sensory field.

The stimuli may be presented in an arrangement that causes them to appear perceptually as being spatially frequency doubled. The stimuli may be presented so as to produce a perception of a spatially frequency doubled arrangement. The stimuli may be presented in an arrangement which produces perceived spatial frequencies that are lower or higher than frequency doubled frequencies. The stimuli may be presented in an arrangement which produces the perception of spatial frequencies between 30% lower than frequency doubled frequencies and 200% of the frequency doubled frequencies. The perceived spatial frequencies may be in the range of 30% to 200% of a spatial frequency doubled perception. The sampling grid may be presented in a polar representation. The stimuli may be chosen such that, in use, each stimulus stimulates approximately equal numbers of sensory cells in the sensory field. The size and shape of individual stimuli for each portion of the visual field may be estimated by computing the spatial autocorrelation in the visual field changes of interest within a polar representation. The coordinates of the polar representation may be linear or nonlinear functions of radius and polar angle.

The method may further comprise the step of enhancing generally elongated features within the polar representation by operation of one or more filters having an aspect ratio of about 3 to 1. The linear filters may comprise running means or Gaussian windows. The one or more filters may be edge preserving filters. The edge preserving filters may be selected from one or more of: median filters, forward-backward median filers, or iterative nonlinear filters.

The method may further comprise the step of recording the responses. The responses may be recorded in a memory. The responses may be recorded either prior to the step of processing of the responses, or post-processing of the responses. The processed responses may be recorded post-processing. The memory may be a memory storage database or device and may be a computer readable memory device.

The responses in the subject's sensory field evoked by the stimuli may be detected by a method selected from the group of: detecting electrical potentials by detecting changes in electric fields and/or potentials for example using an electroencephalograph (EEG) device comprising a plurality of recording electrodes on the scalp of the subject for the detection of cortical potentials evoked by the stimulus; magnetic fields and or potentials for example a similar arrangement to the EEG of recording elements of a magnetoencephalograph (MEG); one or both of electrical or magnetic fields induced by nuclear differential magnetic resonance signals resulting from the flow of deoxyheamoglobin through the nervous system created by sensory nervous system activity; or electromagnetic radiation for example by detecting infrared radiation differentially scattered or absorbed by deoxyheamoglobin or oxyhaemoglobin created by sensory nervous system activity, or a similar arrangement of detection method. Alternatively, the responses in the subject's sensory field evoked by the stimuli may be detected by detecting changes in acoustic signals including acoustic spectroscopy in response to infrared signals influenced by neural processes; by detecting changes in the responses of the subject's pupil or pupils; or by detecting changes in movements of the subject's eye.

The processing may comprise the step of computing linear and/or nonlinear weighting functions that characterise the response of each stimulated portion of the sensory field stimulated by the stimuli. The processing may comprise the step of transforming the recorded responses to a rectilinear representation of the stimulated portions of the sensory field. The processing may comprise the step of transforming the recorded responses to a polar representation of the stimulated portions of the sensory field. The processing may further comprise estimating the size and shape of individual stimuli for each portion of the visual field by computing the spatial autocorrelation in the visual field changes of interest, and transmitting the individual stimuli to the display for presentation to the subject during a sensory field test. The processing may comprise computing the spatial autocorrelation in the visual field changes of interest within a polar representation. The coordinates of the polar representation may be computed as linear or nonlinear functions of radius and polar angle.

The stimuli may be presented on the display either successively or one or more stimuli may be presented concurrently/simultaneously. Concurrently presented stimuli may be presented at statistically independent locations. Concurrently presented stimuli may be presented in a multifocal arrangement. Successive or concurrently presented stimuli may be spatially sparsely presented. Successive or concurrently presented stimuli may be temporally sparsely presented. Successive or concurrently presented stimuli may be sparsely presented both spatially and temporally.

Two or more spatially sparse stimuli may be presented simultaneously. The stimuli may be presented in a multifocal arrangement.

The stimuli may be presented at points on a multi-dimensional sampling grid. The stimuli may be presented at locations on a regular sampling grid. The stimuli may be presented at locations on an irregular sampling grid. The stimuli may be presented at locations on a randomly varying sampling grid.

The sensory field under assessment may be selected from the group of at least one visual sensory field, at least one auditory sensory field, or a tactile sensory field of the subject. The sensory field under assessment may be two or more sensory fields selected from the group of at least one visual sensory field, at least one auditory sensory field, and a tactile sensory field of the subject. The sensory field under assessment may be a combination of any two, three, four, five or more, or all of, the sensory fields selected from the group one or two visual sensory fields, one or two auditory sensory field, and one or more tactile sensory fields of the subject. The sensory field under assessment may be a composite sensory field comprising a subset of the dimensions of those fields, for example the stimulus ensemble spans only the horizontal dimensions of the visual and auditory sensory fields.

The sensory field under assessment may be at least one visual sensory field of the subject. The visual sensory field under assessment may be the visual field sensitivity of one or both retinas of the subject. The method of assessing the visual sensory field of one or both retinas of the subject may be a method for diagnosing a condition causing visual impairment. The method of assessing the visual sensory fields of one or both retinas of the subject may be a method for diagnosing a condition causing localised visual impairment. The condition may be one or more of glaucoma, age-related macular degeneration, or diabetic retinopathy, or localized visual impairments caused by stoke, or neurological disorders such as multiple sclerosis.

According to a second aspect, there is provided an apparatus for assessing the function of at least one sensory field of a subject. The apparatus may comprise a display for presenting stimuli to selected locations of the at least one sensory field. The selected locations may be centred at points on a sampling grid spanning a portion of the sensory field. The stimuli may be adapted such that, if presented simultaneously at the sampling grid points, individual stimuli may overlap in the space defined by the sensory dimensions of the at least one sensory field.

The stimuli presented to the subject's visual field may evoke associated response(s). The apparatus may further comprise a sensor for detecting the responses in the subject's sensory field(s) evoked by the stimuli presented. The individual stimuli may be adapted such that they are individual stimuli sufficiently large, as exemplified by features of interest in the he spatial autocorrelation of the sensory field changes of interest, and smooth sided such that they do not individually represent spatial frequencies higher than those that can be represented by the sampling grid.

The apparatus may further comprise a processor for processing the detected responses. The processing of the detected response may be for relating the detected responses to the function of the subject's sensory field(s) at the selected locations.

In an arrangement of the second aspect, there is provided an apparatus for assessing the function of the sensory field of a subject, the apparatus comprising:

a display for presenting stimuli to selected locations of the sensory field, the selected locations being centred at points on a sampling grid spanning a portion of the sensory field, wherein the individual stimuli if presented simultaneously at the sampling grid points would overlap in the space defined by the sensory dimensions of the field;

a sensor for detecting responses in the subject's sensory field evoked by the stimuli presented; and a processor for processing the detected responses to relate them to the function of the subject's sensory field at the selected locations.

The display may be adapted for presentation of stimuli which may be configured such that, if presented simultaneously, individual stimuli may be sufficiently overlapping such that spatial aliasing of the stimuli on the sampling grid is minimised. That is, the stimuli may transmit little to no spatial frequencies that the sampling grid cannot represent accurately. The stimuli may alternatively or concurrently be configured such that, if presented simultaneously, individual stimuli may be sufficiently overlapping such that they transmit little to no spatial frequencies above the critical sampling frequency of the sampling grid, referred to as the Nyquist rate and defined by the geometry of the sampling grid. The profiles of the stimuli may be smoothly varying. The smoothly varying profiles of the individual stimuli (particularly the edges and/or corners of the profile) may be sufficiently smooth such that they comprise only low spatial frequency Fourier components. The individual stimuli may be blurred. The profiles of the stimuli may be smoothly varying such that the individual stimuli contain only spatial frequencies that are less than or equal to the highest spatial frequency that can be represented by the sampling grid defined by the points of the sampling grid. The sufficiently smooth or blurred individual stimuli have the significant advantage that the subject may not be well refracted (that is, may have incorrect, insufficient or even no refractive correction) without significantly affecting the results of the assessment of the subject's visual field.

The apparatus may be adapted for presentation of stimuli in an arrangement that causes the stimuli to appear perceptually as being spatially frequency doubled. The apparatus may be adapted for presentation of stimuli which produce a perception of a spatially frequency doubled arrangement. The apparatus may be adapted for presentation of stimuli in an arrangement which produces perceived spatial frequencies that are lower or higher than frequency doubled frequencies. The apparatus may be adapted for presentation of stimuli in an arrangement which produces the perception of spatial frequencies between 30% lower than frequency doubled frequencies and 200% of the frequency doubled frequencies. The perceived spatial frequencies may be in the range of 30% to 200% of a spatial frequency doubled perception.

The sensory field(s) under assessment may have a horizontal meridional axis and a vertical meridional axis, and the apparatus may be adapted for presenting individual stimuli which may be adapted such the individual stimuli presented on the display do not overlap with either the vertical or horizontal meridional axes of the sensory field.

The apparatus may be adapted for presentation of the sampling grid in a polar representation. The stimuli may be designed such that, in use, each stimulus stimulates approximately equal numbers of sensory cells in the sensory field. The display of the apparatus may be adapted for presentation of the sampling grid in a polar representation.

The apparatus may further comprise one or more filters for enhancement of generally elongated features with the polar sampling grid. The one or more filters may comprise one or more linear filters which may be running means or Gaussian windows. The one or more filters may be edge preserving filters. The edge preserving filters may be selected from one or more of: median filters, forward-backward median filers, or iterative nonlinear filters.

The apparatus may further comprise a sensor for detection of the responses in the subject's sensory field evoked by the stimuli. The sensor may be selected from the group of: a sensor for detecting electrical potentials by detecting changes in electric fields and/or potentials for example using an electroencephalograph (EEG) device comprising a plurality of recording electrodes on the scalp of the subject for the detection of cortical potentials evoked by the stimulus; magnetic fields and or potentials for example a similar arrangement to the EEG of recording elements of a magnetoencephalograph (MEG); one or both of electrical or magnetic fields induced by nuclear differential magnetic resonance signals resulting from the flow of deoxyheamoglobin through the nervous system created by sensory nervous system activity; or electromagnetic radiation for example by detecting infrared radiation differentially scattered or absorbed by deoxyheamoglobin created by sensory nervous system activity; or a similar arrangement of detection method. The sensor may be a sensor for detecting cortical neural responses from the subject. Alternatively, the responses in the subject's sensory field evoked by the stimuli may be detected by; a sensor for detecting changes in acoustic signals including acoustic spectroscopy in response to infrared signals influenced by neural processes; a sensor for detecting changes in the responses of the subject's pupil; or a sensor for detecting changes in movements of the subject's eye.

The detected responses may be recorded in a memory. The responses may be recorded either prior to the step of processing of the responses, or post-processing of the responses. The processed responses may be recorded post-processing. The memory may be a memory storage database or device and may be a computer readable memory device.

The processor may be adapted for the computing of linear and/or nonlinear weighting functions that characterise the response of each stimulated portion of the sensory field stimulated by the stimuli. The system of any one of the arrangements may The processor may be adapted for transforming the recorded responses to a rectilinear representation of the stimulated portions of the sensory field. The processor may be adapted for transforming the recorded responses to a polar representation of the stimulated portions of the sensory field.

The processor may further be adapted for estimating the size and shape of individual stimuli for each portion of the visual field by computing the spatial autocorrelation in the visual field changes of interest, and may be adapted for presenting the stimuli on the display. The processor may compute the spatial autocorrelation in the visual field changes of interest within a polar representation. The coordinates of the polar representation may be linear or nonlinear functions of radius and polar angle.

The display may be selected from the group of a CRT, LCD, plasma, LED, or OLED image display screen.

The processor may be adapted for presenting individual stimuli on the display either successively or, alternatively, one or more stimuli may be presented concurrently/simultaneously. Concurrently presented stimuli may be presented at statistically independent locations. Concurrently presented stimuli may be presented in a multifocal arrangement. Successive or concurrently presented stimuli may be spatially sparsely presented. Successive or concurrently presented stimuli may be temporally sparsely presented. Successive or concurrently presented stimuli may be sparsely presented both spatially and temporally.

The apparatus may be adapted for simultaneous presentation of two or more spatially sparse stimuli. Alternatively, the apparatus may be adapted for presentation of the stimuli in a multifocal arrangement.

The apparatus may be adapted for simultaneous presentation of the stimuli at points on a multi-dimensional sampling grid. The stimuli may be presented at locations on an regular sampling grid. The stimuli may be presented at locations on an irregular sampling grid. The stimuli may be presented at locations on a randomly varying sampling grid.

The apparatus may be adapted for assessment of a sensory field which may be selected from the group of at least one visual sensory field, at least one auditory sensory field, or a tactile sensory field of the subject. The apparatus may be adapted for assessment of two or more sensory fields, which may be selected from the group of: at least one visual sensory field, at least one auditory sensory field, and at least one tactile sensory field of the subject. The apparatus may be adapted for assessment of a sensory field which may be a combination of any two, three, four, five or more, or all of, the sensory fields selected from the group one or two visual sensory fields, one or two auditory sensory field, and one or more tactile sensory fields of the subject. The apparatus may be adapted for assessment of a sensory field which may be a composite sensory field comprising a subset of the dimensions of those fields, for example the stimulus ensemble spans only the horizontal dimensions of the visual and auditory sensory fields.

The apparatus may be adapted for assessment of at least one visual sensory field of the subject. The visual sensory field under assessment may be the visual field sensitivity of one or both retinas of the subject. The apparatus may be adapted for assessing the visual sensory field of one or both retinas of the subject and may be adapted for the diagnosis of a condition causing visual impairment. The assessment of the visual sensory field of one or both retinas of the subject may be adapted for diagnosis of a condition causing localised visual impairment. The condition may be one or more of glaucoma, age-related macular degeneration, or diabetic retinopathy in, or localized visual impairments caused by stoke, or neurological disorders such as multiple sclerosis affecting one or both eyes of the subject.

In a third aspect, there is provided a system for the assessment of the function of a at least one sensory field in a subject, the system comprising an apparatus of the second aspect, wherein the apparatus is adapted for execution of the methods of the first aspect.

In a fourth aspect, there is provided a use of the apparatus or system of the second or third aspects for assessment of one or more sensory fields of a subject. The sensory field(s) under assessment may be a visual sensory field and the assessment may be assessment of any one of more of glaucoma, age-related macular degeneration, diabetic rectinopathy, stroke or multiple sclerosis affecting one or both eyes of the subject.

The use of the apparatus or the system of the second or third aspects respectively may be accordance with the method of the first aspect for assessment of one or more sensory fields of a subject. The sensory field(s) under assessment may be a visual sensory field and the assessment may be assessment of any one of more of glaucoma, age-related macular degeneration, diabetic rectinopathy, stroke or multiple sclerosis affecting one or both eyes of the subject.

The aspects of the invention disclosed herein provide for improved methods for the assessment and quantification of the sensory fields field of human and animal subjects, particularly the visual fields of eyes, and apparatus and systems for carrying out the improved assessment methods. Although mainly useful for detecting changes in visual sensitivity due to disease processes such as glaucoma, diabetic retinopathy (DR) or age-related macular degeneration (AMD) the method may also be used to determine such things as the location of the normal blind spot, the absolute limits of the visual field for particular normal persons imposed by skull shape, or reversible changes in the visual field as might occur in various forms of stress testing, or as a function of growth of the head, or neurological changes over the course of normal childhood development. The methods may also be used for assessment of localized visual impairments caused by stoke, or neurological disorders such as multiple sclerosis. Nevertheless the examples given herein mainly relate to persons with the eye disease glaucoma because of the readily available variants of visual field sensitivity that they can present. It will be appreciated, however, that that the methods and apparatus described herein are also applicable to other causes of loss of visual sensitivity such as age-related macular degeneration, diabetic rectinopathy, stroke or multiple sclerosis.

The aspects of the invention disclosed herein are equally applicable to standard behaviourally mediated perimetry or to multifocal methods for mapping the visual fields. More generally the method may readily extend to the assessment of other sensory fields such as fields defined on two tactile dimensions, or auditory and visual dimensions, or any combination or number of such sensory dimensions. Irregular sampling grids have several advantages, particularly the ability to estimate the power, if not the phase, of frequency components of the sensory field that would be beyond the normal Nyquist rate.

It has been found by the inventors that visual fields may contain regions where the changes in sensitivity vary rapidly over visual space and that these rapidly changing sensitivity regions cause the combination of small test stimuli and coarse spatial sampling used in current permitters to transform these high spatial frequencies into distortions of the measured visual fields by aliasing. The ubiquitous nature of these design deficiencies indicates strongly that persons skilled in the art surprisingly do not recognise potential problem of aliasing in standard visual field test apparatus. Accordingly, in arrangements of the aspects disclosed herein, it is realised that modification of the visual stimuli used for quantifying the visual field such that they are designed so at to overlap when presented at adjacent locations in the particular sampling grid, and should have blurred edges, provides significant advantages over commonly used methods and apparatus. The combination of large size relative to the sample grid and edge blurring has been found to prevent the potentially distorting effects of high spatial frequencies that cannot be reliably represented by the density of the sampling grid, whether that grid is regular or random.

A further significant advantage of the methods and apparatus disclosed herein is that by having many stimuli that would overlap if presented simultaneously, a particular stimulus might overlap more exactly with a given patch of visual field sensitivity change, thereby maximizing the ability of that stimulus to identify a localized difference in sensitivity.

Through further consideration of the anatomy of retinal ganglion cells, in particular the paths their axons take to the optic nerve head or disc, and the fact that each half the occipital visual cortex only represents the left or right half of the visual field, it is realised that that steps of visual sensitivity that are defined along the horizontal and vertical meridians of the visual field are not uncommon. Therefore, while the stimuli should potentially overlap with each other, it has been found that in particular arrangements of the methods and apparatus for visual field assessment, particularly arrangements of the visual stimulus ensembles that do not overlap or cross these meridians, the ability to detect such meridional steps of visual sensitivity may be maximised.

In a further aspect, it is recognised by the inventors that polar maps of the visual field are more suited to characterising patchy changes in sensitivity of the retina. Thus, if maps of the visual field obtained with different sampling grids are to be transformed to a single standardised representation for the purposes of comparing the differently measured fields, significant advantages in the analysis of the visual field may be achieved if the that representation is a standard polar representation. This also permits measures such as the spatial autocorrelation function of visual field changes to be determined in a relevant coordinate system to determine optimal stimulus size at each visual field location. Such polar representations of the visual field are of particular utility in glaucoma where common changes to the sensitivity of the visual field map to largely rectangular shapes or simple linear gradients that can be easily recognized. Finally, radial representations are recognised to give appropriate weight to the central visual field and polar stimuli are able to be designed such that each individual stimulus stimulates an approximately equal number of sensory cells.

In one particular arrangement, there is provided a method for assessing the functional status of component parts of the sensory field of a subject, the method comprising:

(a) presenting stimuli to individual parts of the sensory field centred at points on a potentially multi-dimensional, regular or irregular, sampling grid spanning the portion of the sensory field that is of interest, where the individual stimuli are sufficiently large and have sufficiently smoothly varying profiles that they do not transmit frequencies found within the multi-dimensional sensory field, that are higher than those that can be represented accurately by the density of the sampling grid, and so if presented together at the sampling grid points the individual stimuli would overlap in space;

(b) overlapping more stimulus positions than would be required to significantly reduce aliasing effects sampling so that particular stimuli may overlap well with a given patch of changed sensitivity of the sensory field.

The size and shape of each stimulus for characterization of the visual field may be chosen with regard to the radial symmetry and higher foveal density of the sensory neurons of the retinally associated visual cortex or thalamic visual area. The size and shape of each stimulus for characterization of the visual field may be chosen such that each individual stimulus stimulates approximately the same number of sensory neurons of the retinally associated visual cortex or thalamic visual area.

The optimal size and shape of individual stimuli for each part of the visual field may be estimated by computing measures such as the spatial autocorrelation in the visual field changes of interest within a polar representation of visual field data where the coordinates of the transformed space may be linear or nonlinear functions of radius and polar angle.

The sizes of the stimuli may be larger than would be predicted as being optimal from analysis in a polar space given that in a measurement situation the signal to noise ratio available, especially in damaged fields may be lower.

The overlapping and smoothly varying (i.e. sufficiently smoothed or blurred) stimuli may display the spatial frequency doubling illusion. The overlapping and blurred-edged stimuli may display higher spatial frequencies than the actual stimulus spatial frequency. The higher spatial frequencies may be higher than twice the actual stimulus spatial frequency. By virtue of a preponderance of low spatial frequency content, the higher spatial frequencies may be generally below 1 cpd. The overlapping and blurred stimuli may be coupled with temporal modulations selected from the group of rapid contrast reversal, rapid onset and offset, or rapid translation across the visual field within a region of the visual field. The temporal modulations may cause the stimuli to be modulated at a rate of between 10 to 30 Hz, but may contain other frequencies as well in any range providing they make up a relatively small proportion of frequencies in the stimulus.

In particular arrangements, the individual stimuli may have insufficiently blurred profiles or insufficient overlap such that they transmit some frequencies of interest providing the sampling grid was suitably random to permit estimation of the power of frequencies in the sensory field that would be above the normal Nyquist rate defined by the sampling grid density.

In use, the individual stimuli may be presented individually to each part of the visual field of a subject undergoing a visual field assessment. Behavioural responses of the subject may be determined for stimuli presented to each location. The behavioural responses may be a button press by the subject. A threshold of minimum contrast or intensity of the stimuli may be determined for each stimulus location. The frequency of seeing a supra-threshold stimulus may be determined for each stimulus location.

The method of presentation of the stimuli may be multi-focal, wherein each stimulus at its location is be modulated by temporal sequences. The temporal sequences may be sufficiently statistically independent to permit estimation of linear and non-linear weighting functions adapted to characterisation of measured responses to each stimulus presented to each part of the nervous system of the subject under test. The measured responses may provide estimates of the response of the nervous system of the subject under test to each stimulus. The measured responses may including responses to interactions between a given stimulus sequence and itself at different delays. The measured responses may include interactions a stimulus at a first location and at least one other stimulus other locations and at several delays. The measured responses may be estimated from objectively measured detection and recordings of neural activity from the nervous system. The measured recordings may be detected and/or recorded by a suitable sensor and/or recorder as required. The sensor may be selected from the group of an electrical or magnetic sensor; a sensor suitable for detecting changes to the absorption, scattering or polarization infrared or other electromagnetic radiation; a functional magnetic resonance imaging sensor; or a sensor for detecting responses of the subject's pupil or pupils. The detected responses may then be recorded in a suitable recorder such as a memory device.

The visual field sensitivity may be transformed to a polar representation, such that localized changes to the visual field sensitivity may be readily identified. The polar representation may provide analysis for recognition of visual field changes in the polar domain. Data from various perimetric sampling strategies may be transformed into a standard polar representation for the comparison of data that would otherwise be described on different sampling grids.

BRIEF DESCRIPTION OF THE DRAWINGS

Arrangements of the methods, apparatus and systems will now be described, by way of an example only, with reference to the accompanying drawings wherein:

FIGS. 5A and 5B respectively show an image and contour plot of a single two degree-wide blurred visual field stimulus;

FIG. 5C is a graph of the amplitude of an ensemble of the stimuli of FIG. 5A arrayed in the visual field sampling grid of FIG. 5D taken along line A-A, FIG. 5C showing the degree of overall overlap between adjacent stimuli that would occur if a set of such stimuli were set out on a sampling grid that sampled visual space at 1 degree intervals horizontally and vertically;

FIGS. 10A to 10C respectively show an image, contour plot and amplitude distribution of an example of a square visual field stimulus with blurred edges of width 9 degrees for use in an HFA 30-2 test pattern with a 6 degree sampling;

FIGS. 15A and 15B respectively show an example visual field as measured with a HFA 24-2 pattern in rectilinear and polar representations;

FIGS. 16A and 16B respectively show rectilinear and polar representations of a further example visual field with glaucomatous damage;

FIGS. 17A and 17B respectively show rectilinear and polar representations of a further example visual field with glaucomatous damage;

FIGS. 18A and 18B respectively show rectilinear and polar representations of a further example visual field with glaucomatous damage;

DETAILED DESCRIPTION OF THE PREFERRED EMBODIMENTS

Unless defined otherwise, all technical and scientific terms used herein have the same meaning as commonly understood by those of ordinary skill in the art to which the invention belongs. For the purposes of the present invention, the following terms are defined below.

The articles "a" and "a" are used herein to refer to one or to more than one (i.e. to at least one) of the grammatical object of the article. By way of example, "an element" refers to one element or more than one element.

The term "about" is used herein to refer to quantities (e.g. frequencies or probabilities) that vary by as much as 30%, preferably by as much as 20%, and more preferably by as much as 10% to a reference quantity or quantities.

Throughout this specification, unless the context requires otherwise, the words "comprise", "comprises" and "comprising" will be understood to imply the inclusion of a stated step or element or group of steps or elements but not the exclusion of any other step or element or group of steps or elements.

Although any methods and materials similar or equivalent to those described herein can be used in the practice or testing of the present invention, preferred methods and materials are described. It will be appreciated that the methods, apparatus and systems described herein may be implemented in a variety of ways and for a variety of purposes. The description here is by way of example only.

Figure 1:
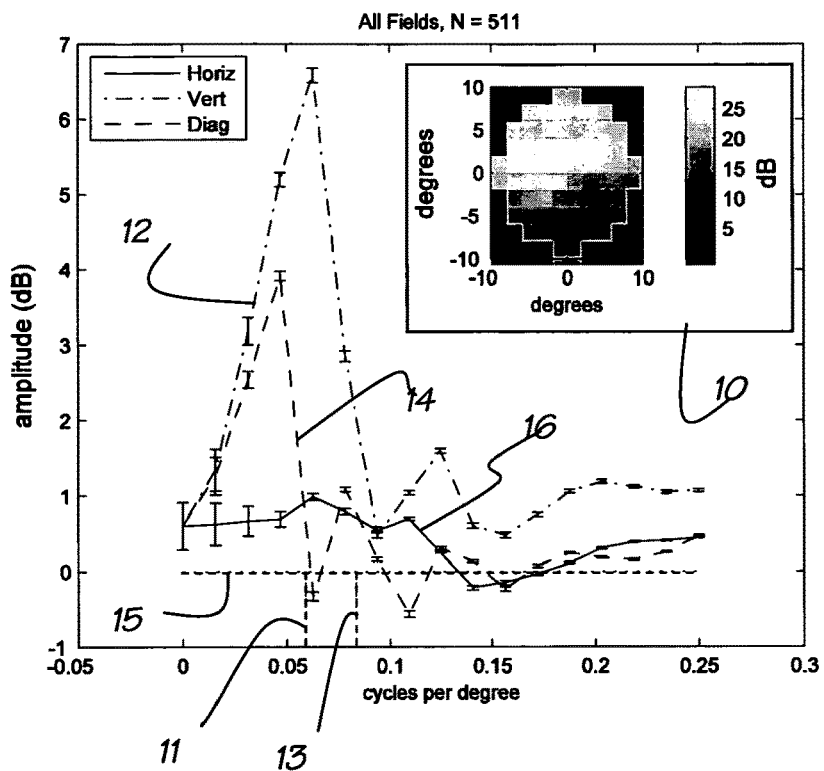
FIG. 1 is a graph of three transects though the average difference spectra showing the additional spatial frequencies that occur above the Nyquist rates for the more common and spatially coarser 24-2 and 30-2 tests, with the mean of 511 HFA 10-2 visual field tests used to compute the spectra shown in the insert.

Referring to FIGS. 1 to 4, it can be see that current perimeter designs exhibit undersampling and aliasing effects due to the presence of spatial frequencies above $S_c$ as defined by their sampling lattice. In particular, referring to FIG. 1 based on the measurement of 511 HFA 10-2 visual fields obtained from many different subjects. The 10-2 pattern is an optional test pattern that has a square lattice of test points separated horizontally and vertically by 2 degrees, 3 times finer than the standard test grid. Thus, $S_c$ for the finer grid is 3 times higher making it possible to see if frequencies in visual field sensitivity exist above $S_c$ for the standard, coarse, 6 degree grid. The insert 10 at top right of FIG. 1 shows the mean sensitivity across the visual field of the measured fields (511 in total) from a sample of patients with glaucoma. Glaucoma is a disease that in its earlier stages produces localized damage to the retina leading to localized visual impairment or blindness. Localized blind regions of the visual field are referred to as scotomas. The three traces 12, 14 and 16 of FIG. 1 are respectively the horizontal, vertical and diagonal transects through functions derived from the 511 two dimensional amplitude spectra of the 511 measured visual fields. These derived functions will be referred to as the difference spectra.

As shown in inset 10 of FIG. 1 all the fields are bounded by a roughly circular window of 10 degrees radius. This windowing will cause some artefacts with higher spatial frequencies in the spectra. To minimize this effect one dummy field was constructed for each actual glaucomatous visual field. The dummy fields had the exact shape of the circular window of the real fields, where each point in the dummy field was replaced with the mean of points from a given real field. Thus, for each real field, its dummy had the same mean sensitivity value as that real field. The amplitude spectra from each of the 511 dummy fields were then computed. Notice that these dummy fields have all the spatial properties of the real field except for any structure within the field. The difference spectra were then formed by subtracting the dummy spectra from each of their corresponding real field spectra. The difference spectra thus indicate any extra frequencies that would not be predicted from a flat circular field.

FIG. 1 shows two vertical dotted lines 11 and 13 below the horizontal dotted line 15 that marks zero (0) amplitude. The left vertical line denotes the $S_c$ for the diagonal separation of a 6 degree sample grid, $1/(12*\sqrt{2})$ cycles per degrees (cpd). The right vertical line denotes the $S_c$ for the horizontal and vertical directions, 1/12 cpd. The three traces 12, 14 and 16 illustrate the mean frequency content of the difference spectra. The error bars are standard errors. The very small error bars, especially at frequencies above $S_c$ for the 6 degree sample grid, indicate these frequencies are almost all highly significantly differently different from zero amplitude. As can be inferred from the mean field presented in the insert 10, many of the fields of the glaucoma subjects showed a step in sensitivity at the horizontal meridian of the field which is common in glaucoma. The step would enhance increase the high spatial frequency content in the vertical direction. This is demonstrated by the mean vertical transect through the difference spectra (trace 12). This effect is minimized by considering transects corresponding to the horizontal meridian of the difference spectrum (trace 16), any such frequencies being orthogonal to the step of sensitivity in the fields. The diagonal transect through the difference spectra (trace 14) will also be less affected by any horizontally oriented steps in the fields.

Figure 2:
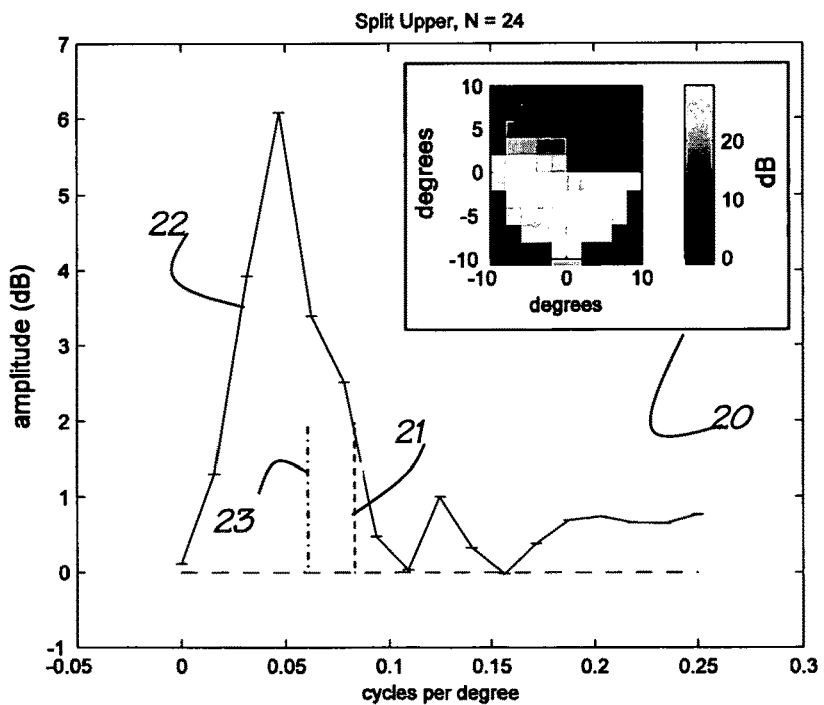
FIG. 2 shows a graph of the mean of the vertical, horizontal and diagonal transects through the mean difference spectrum for 24 HFA 10-2 visual fields with a superior field defect showing a step at the horizontal meridian.
Figure 3:
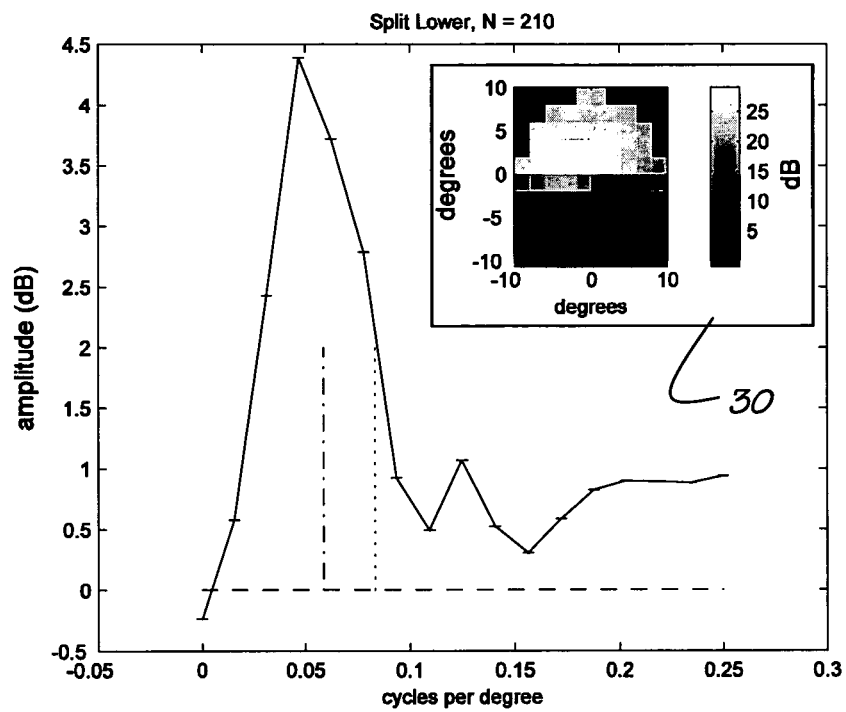
FIG. 3 shows a graph of the mean of the vertical, horizontal and diagonal transects through the mean difference spectrum for 210 HFA 10-2 visual fields with an inferior field defect showing a step at the horizontal meridian.
Figure 4:
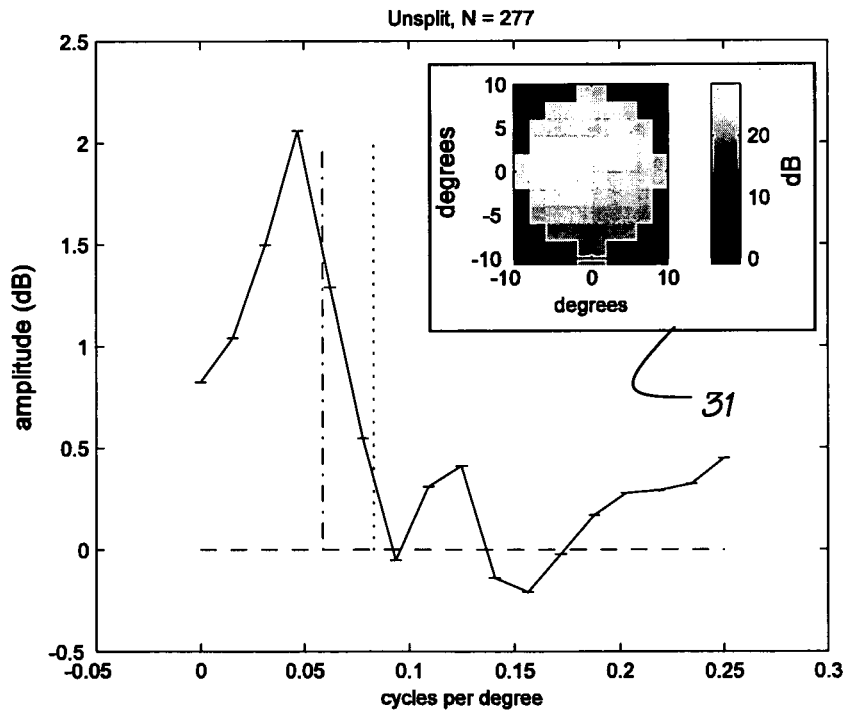
FIG. 4 shows a graph of the mean of the vertical, horizontal and diagonal transects through the mean difference spectrum for 277 HFA 10-2 visual fields with no significant step at the horizontal meridian.

Another way to examine the relative contribution of visual field steps is to compare difference spectra for fields that do or do not contain definite steps. FIG. 2 shows the results for the 24 fields that had sensitivity suppression in the superior visual field that produced a step. Again the mean real glaucomatous field is given in the insert 20 at top right. Trace 22 of FIG. 2 shows the mean of the horizontal, vertical and diagonal transects through mean difference spectrum of FIG. 1. The dashed and dot-dashed vertical lines (21 and 23 respectively) indicate the $S_c$ values for the 6 degree sample grid. FIG. 3 shows the mean of the horizontal, vertical and diagonal transects through mean difference spectrum of 210 measured glaucomatous visual fields that showed a vertically inverted step as can be seen in insert 30. FIG. 4 shows the mean of the horizontal, vertical and diagonal transects through mean difference spectrum of for 277 glaucomatous fields that had no distinct step, as can be inferred from the mean field in the insert 31. Even here frequencies exist well above the Nyquist rate, $S_c$, for the 6 degree grid.

It is significant that these test data came from an HFA test instrument that used the same methods that are used in the standard 24-2 test. It is clear that frequencies of modulation of the visual field across space exist well above the Nyquist rate for the 6 degree sample grid. As mentioned above these higher frequencies will appear in the band 0 to $S_c$ as lower, aliased, spatial frequencies. Note that this folding back will occur at least three times since the visual field modulation extend to frequencies about 3 times the Nyquist frequency. The amplitudes of the super-Nyquist frequencies are around 1 dB. Since multiple fold backs occur this can multiply the amplitude of the resulting distortion patterns. The various frequencies can add constructively depending on their phases. Overall then, false patterns that could distort the fields can occur with amplitudes around 6 dB. Static perimeters are noted for their poor reproducibility, which becomes worse as visual fields become more damaged. It is possible that this damage is creating higher spatial frequency modulations of the visual field and these increasingly large high frequency components are tending to distort the measured fields, possibly contributing to the lack of reproducibility.

Large Overlapping Stimuli with Low-spatial Frequency Content

FIG. 5A shows a potential stimulus for a perimeter. In this case the stimulus is a two dimensional Gaussian shaped spot of light. FIG. 5B shows the same stimulus as a contour plot, where the contours are in steps of 10% of the maximum brightness of the stimulus. FIG. 5D shows an ensemble of these Gaussian stimuli arranged in a regular square grid. The grid points are separated by 1 degree of visual angle. FIG. 5D represents the possible positions of the perimetry stimulus across the visual field. FIG. 5C is a horizontal transect through the ensemble at 0 degrees elevation showing that at this separation the Gaussian stimuli would overlap.

Figure 6:
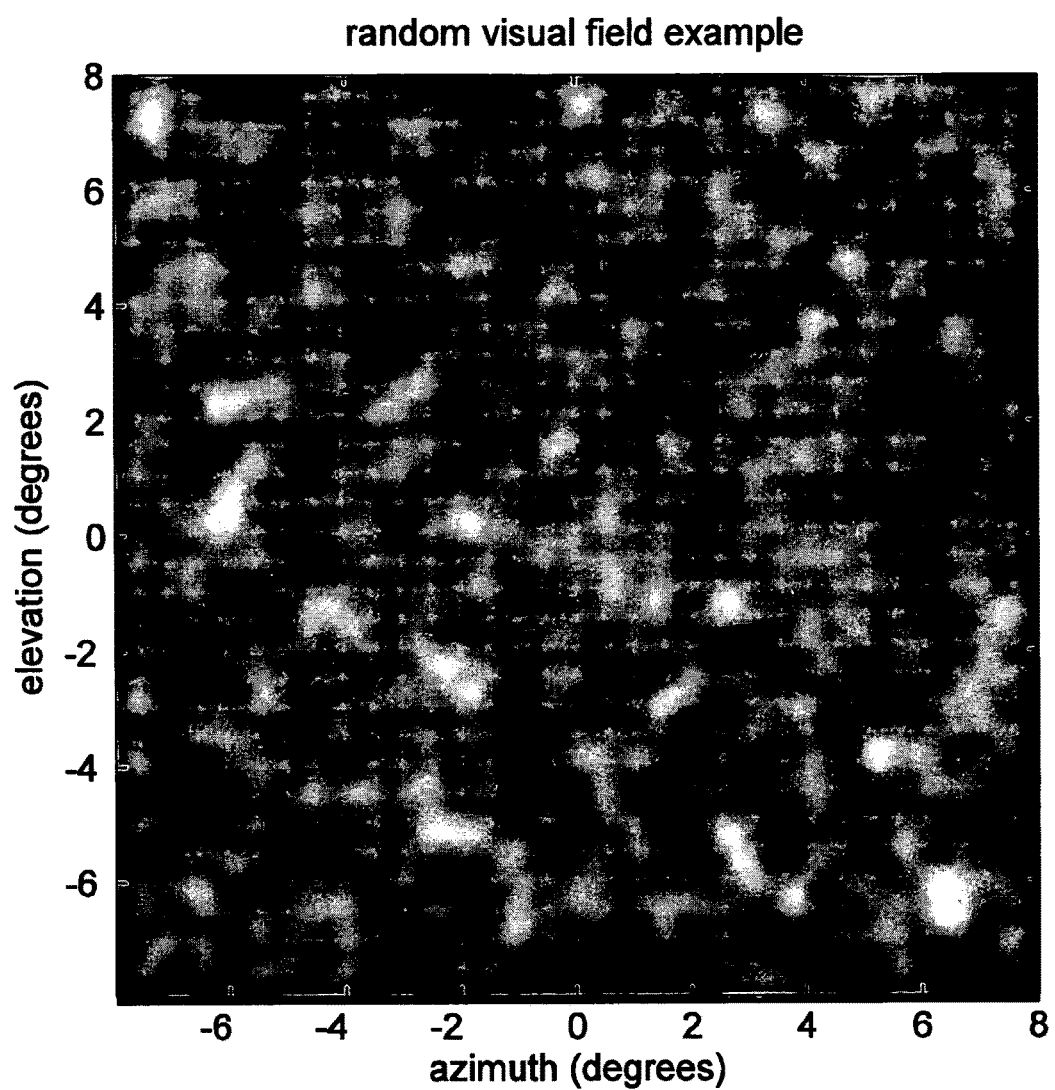
FIG. 6 shows an example of a model visual field containing high frequency spatial modulations of sensitivity that vary more rapidly across space than a 1 degree sampling grid similar to that of FIG. 5D can accurately represent.
Figure 7A:
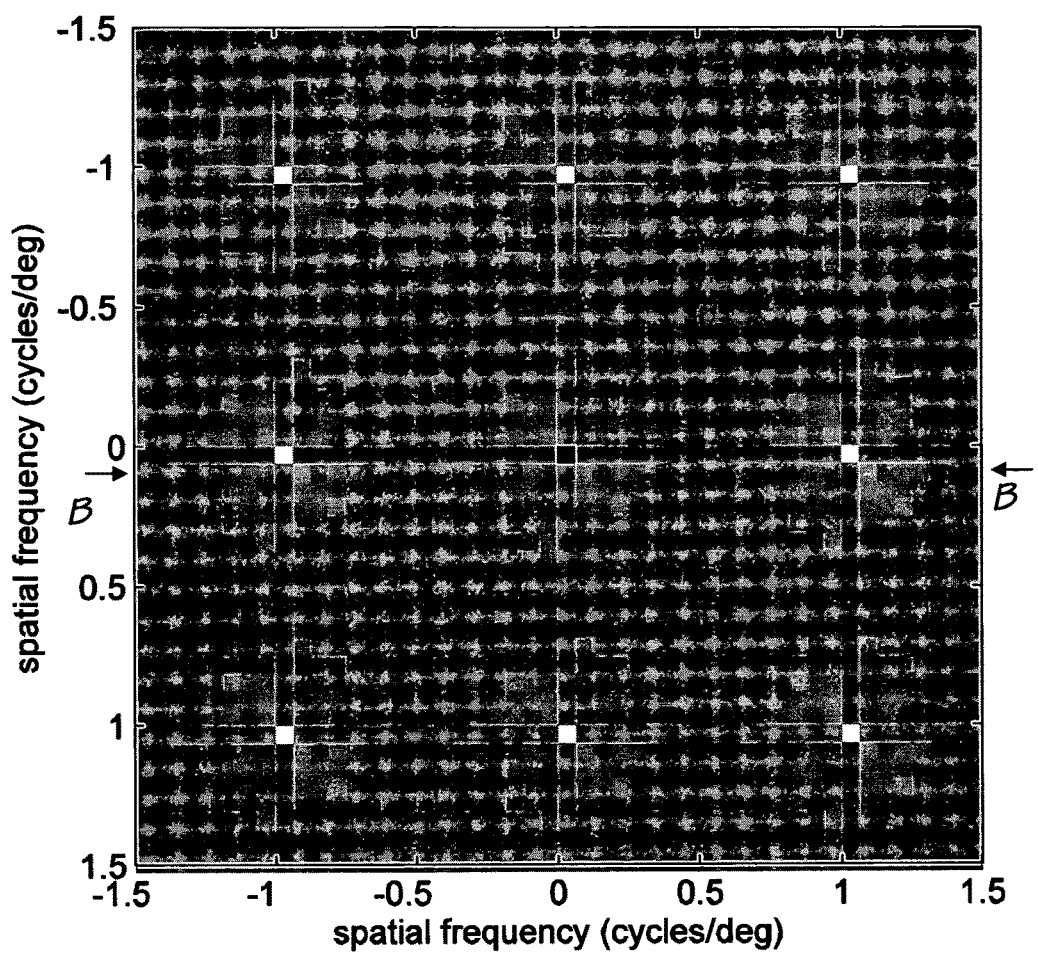
FIG. 7A shows an example of aliasing in a two dimensional amplitude spectrum of a visual field similar to that of FIG. 6 containing high spatial frequencies following sampling by the stimuli of FIG. 5A and arranged in the sampling grid of FIG. 5D.
Figure 7B:
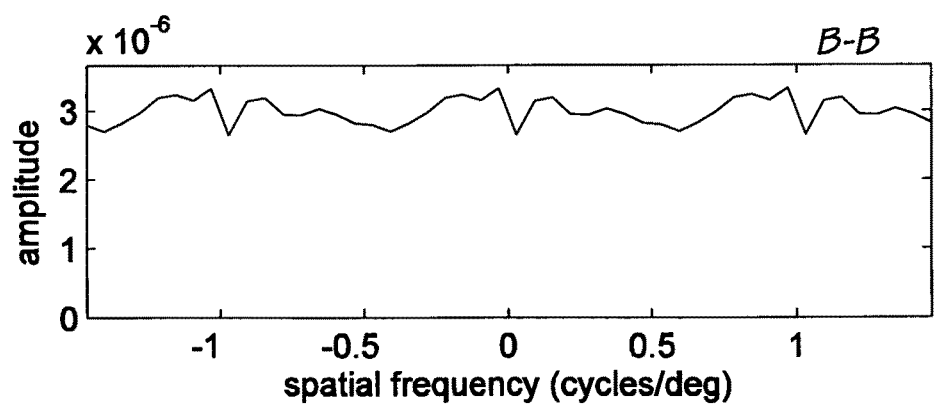
FIG. 7B is an amplitude cross section of the amplitude spectrum of FIG. 7A taken near zero cycles/degree along line B-B.

FIG. 6 shows a model random visual field which contains spatial frequencies higher than those in the modulations of the Gaussian stimuli. Persons skilled in the art will understand that sampling the visual field with stimuli similar to that of either FIG. 5D or FIG. 6 will result in a two dimensional spatial frequency spectrum that contains low pass filtered copies spectrum of the visual field spaced at intervals 2 times the Nyquist rate, in this case at intervals of 1 cpd. If the sample grid is too coarse for the frequency content of the spectrum of the fields then high frequencies in the copies of the spectrum of the visual field will add to low frequencies in the main spectrum, this is the source of aliasing. An example spectrum is shown in FIG. 7A and a horizontal transect through the spectrum at A-A near 0 cpd is shown in FIG. 7B showing that the overlap of the spectra is very large producing abundant aliased frequencies. As suggested above, making the perimetric stimuli larger and more smooth sided should moderate this effect which could seriously distort the measured visual field. It can clearly be seen that the narrow, and so relatively spatially sharp, stimuli and coarse square sampling lattice cause copies of the spectrum of the visual field to overlap, thus high spatial frequencies beyond the Nyquist rate, here 0.5 cycles per degree horizontally and vertically, causing frequencies from higher order copies to leak into the main spectrum, appearing as lower "aliased" spatial frequencies that could distort the measured visual field.

The effects of sampling with a regular grid highlight the possible advantages of sampling with an irregular, random grid. The main advantages are that for a two dimensional sensory field aliased frequencies are scattered into a ring spectrum that is uniformly distant from the origin and the aliased frequencies have random phases that may be less likely to add constructively. For higher dimensional sensory fields the ring will be a multi-dimensional sphere. Moreover, if only the power and not the phase, of the frequency spectrum of the sensory field are required this can be done up to arbitrarily high frequencies provided the sampling gird is suitably random. Although this is predicated on sampling in the time domain, it is reasonable that the concepts can readily be extended to multiple dimensions.

This opens up the possibility that the sampling grid could be random and possibly changing within the region of the sensory field of interest during the course of a testing session, again minimizing the effects of aliasing and potentially providing accurate information on the power of higher frequencies in the sensory field beyond the normal Nyquist rate. This information may be useful in characterizing departures from population norms caused either by diseases such as glaucoma or by such normal process as belonging to particular racial groups of humans or species of animals with differing skull shapes that determine the limits of the visual field, or reversible changes in sensory fields imposed by various forms of stress testing in normal humans, or changes that occur with normal childhood development.

Figure 8A:
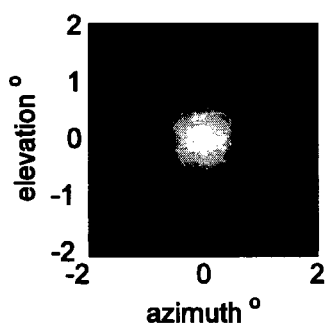
FIGS. 8A and 8B respectively show an image and contour plot of a single two degree-wide blurred visual field stimulus of twice the angular width as the stimulus of FIG. 5A.
Figure 8B:
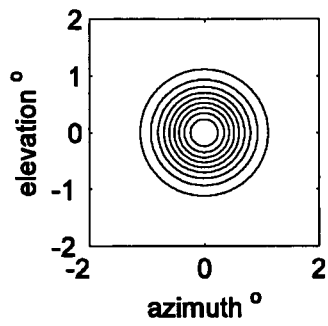
Figure 8C:
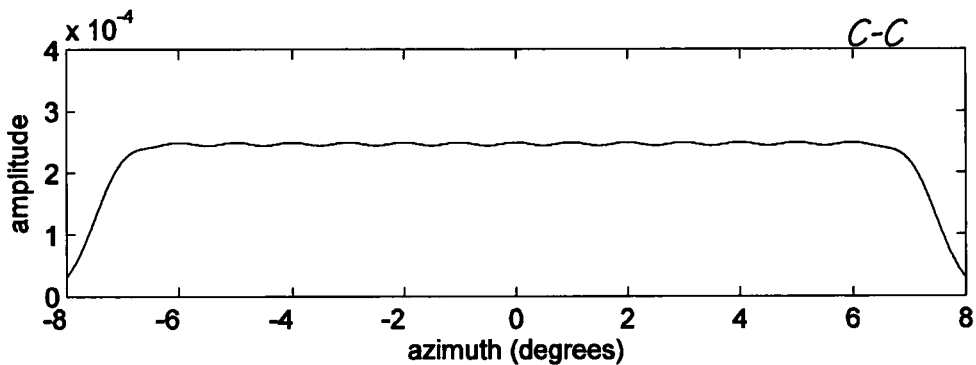
FIG. 8C is a graph of the amplitude of an ensemble of the stimuli of FIG. 8A arrayed in the visual field sampling grid of FIG. 8D taken along line C-C, FIG. 8C showing the degree of overall overlap between adjacent stimuli that would occur if a set of such stimuli were set out on a sampling grid that sampled visual space at 1 degree intervals horizontally and vertically.
Figure 8D:
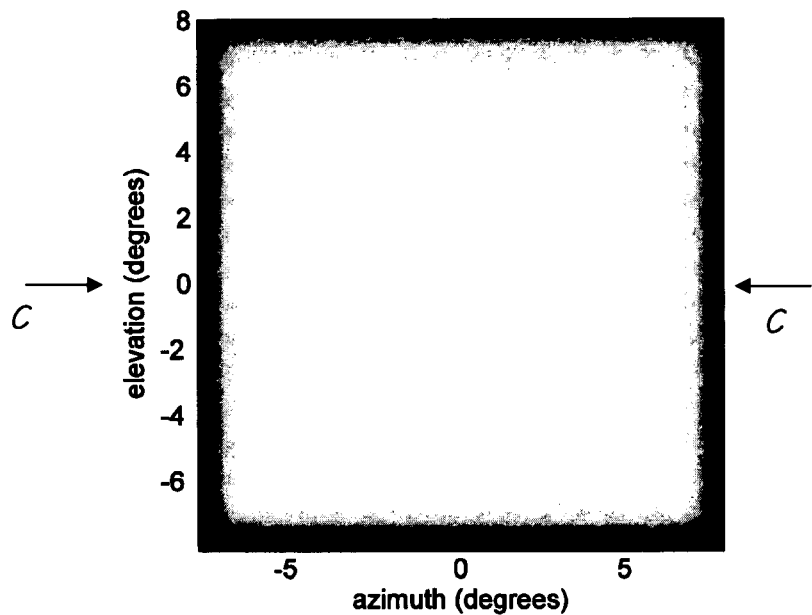
Figure 9A:
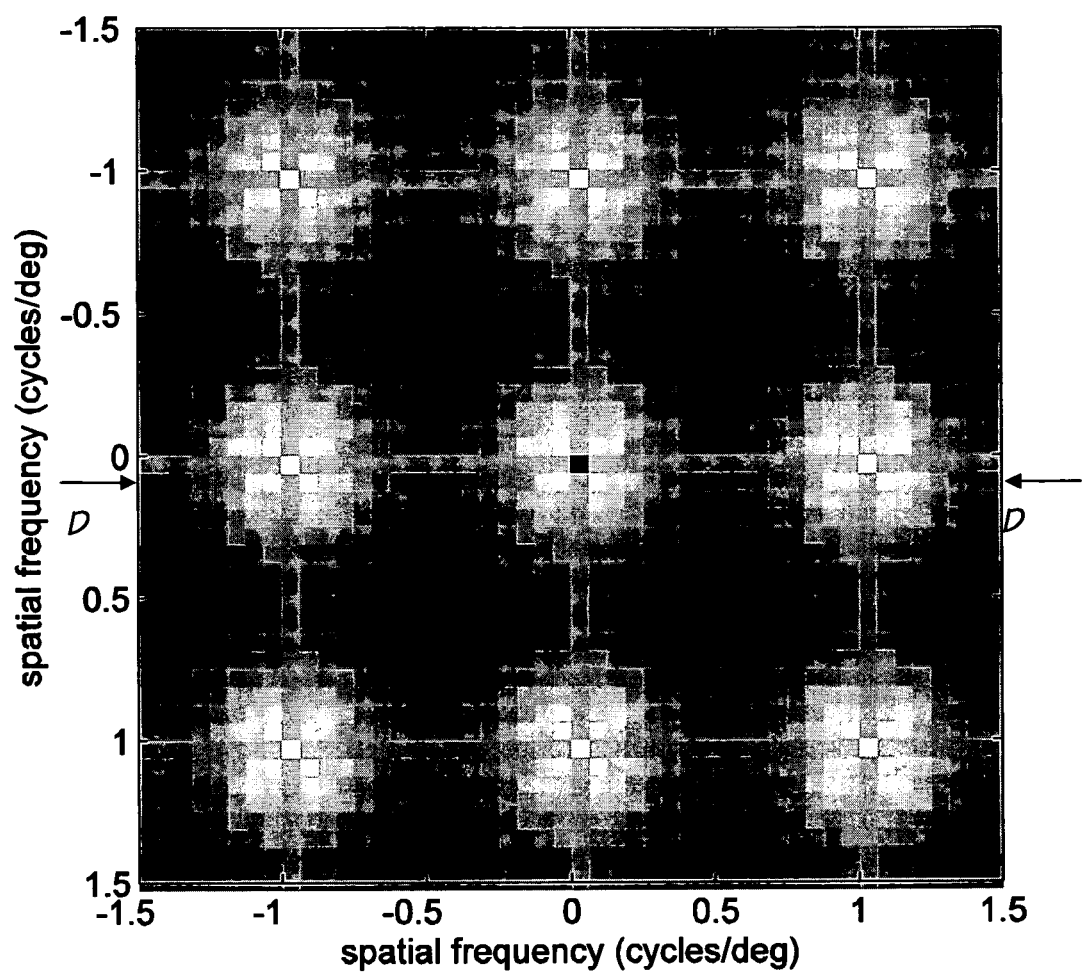
FIG. 9A shows an example of aliasing in a two dimensional amplitude spectrum of a visual field test stimulus similar to that of FIG. 6 containing high spatial frequencies following sampling by the stimuli of FIG. 8A and arranged in the sampling grid of FIG. 8D.
Figure 9B:
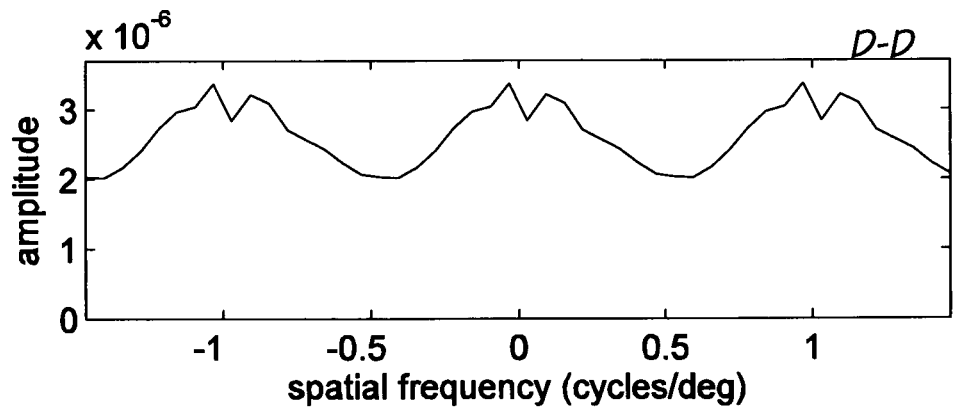
FIG. 9B is an amplitude cross section of the amplitude spectrum of FIG. 7A taken near zero cycles/degree along line D-D.

FIGS. 8A and 8B show Gaussian stimuli that are twice as large as those in FIG. 5. When placed at the same 1 degree intervals as in FIG. 5, FIG. 8C shows that the overlap of the stimuli, if they were to be presented simultaneously, is almost complete. Nevertheless the anti-aliasing filtering effects of these larger stimuli is still not quite sufficient to separate the copies of the spectrum as shown in the amplitude spectrum of FIG. 9A, indicating that the effects of aliasing still occur. The larger stimuli of FIG. 8 have reduced the amplitude of the super-Nyquist spatial frequencies but not enough to prevent aliasing. This illustrates the need for substantial overlap of the blurred stimuli to reduce aliasing and it has been found that a quite large overlap relative to the sample grid's spacing is required to eliminate this distorting effect. The exact overlap will depend on the spatial frequency content of the stimuli and the visual field, i.e. of the anti-aliasing filters. For stimuli that have a spatially low-pass spatial frequency spectrum, the overlap should minimally be such that adjacent stimuli touch at half height and can extend to 5 or more times the average distance between sampling locations in the grid. Of course the effect will be less when the modulations of the visual field are not as rapid as in the examples used here (FIG. 6).

Broadly therefore, a method that has been found to provide significant advantages in overcoming spatial aliasing in visual fields is to make the test stimuli much larger than that used in conventional perimeters and for the stimuli to have smoothed edges. These larger, smooth-edged, stimuli spatially filter the visual field, effectively removing shorter range fluctuations of the visual field, thus eliminating aliasing effects. Note that smoothing after sampling, as partially done by the linear interpolation of grey scale plots of thresholds on HFA reports, does not fix the problem of aliasing because by that time all frequencies above $S_c$ have already been translated into aliased frequencies below $S_c$. Smoothing must occur in the sampling process or before.

Current perimeter designs, in not having any form of anti-aliasing filter, therefore are thus tacitly predicated on the concept that there are no spatial frequencies above $S_c$ as defined by their sampling lattice.

Thus, due to the presence of higher spatial frequencies than the Nyquist rate for the standard 6 degree perimeter grid within glaucomatous visual fields it has been found that overlapping stimuli provides significant advantages in the assessment of the visual field by minimising the effects of aliasing. Beyond the beneficial effects of reducing aliasing, the use of overlapping stimuli for perimetry also has additional significant advantages such as it enables the restoration of some of the utility of dynamic perimetry, because with many translations of a single stimulus there is the prospect of one stimulus occurring in the optimum position to identify a localized region of damage. This leads to the question: what is the optimum size or shape for the stimuli?

The anatomy of the eye itself is used for determining the optimum stimulus shape for a given part of the visual field. For example, in the case of the disease glaucoma, the disease causes the progressive loss of the retinal ganglion cells whose nerve fibres, also called axons, make up the optic nerve. These cells are at their densest at the fovea and their density falls with retinal eccentricity outward from the fovea. The density function of eccentricity, ecc, D(ecc) is closely approximated by $D(ecc)=a(c+ecc)^{-z}$ where the exponent z is typically about 2 or less, where c governs the foveal retinal density and z the extrafoveal roll-off in density with increasing retinal eccentricity, a is just an overall scaling factor [the relationship between D(ecc) and the Nyquist rate at each eccentricity is discussed in T. Maddess et al "Evidence for spatial aliasing effects in the Y-like cells of the magnocellular visual pathway", *Vision Research*, Volume 38, Pages 1843-1859, 1998]. The high central density of retinal ganglion cells implies that that if glaucoma creates two scotomas of the same size, one in peripheral retina, and one in central retina, then the central scotoma has been produced by the death of many more retinal ganglion cells. For this reason central scotoma are generally regarded as more diagnostic of serious glaucoma [see for example E. Hodapp, et al, "The asymptomatic patient with elevated pressure", *Clinical decisions in glaucoma*, Pages 52-61, 1993].

Several other methods of grading of the severity visual field damage by glaucoma also give extra weight to the central visual fields, notably the Glaucoma Hemifield Index of the Humphrey Field analyser, and grading schemes based on that such as the "structure and function evaluation" (SAFE) method [see C. A. Johnson, et al, "Structure and function evaluation (SAFE): I. criteria for glaucomatous visual field loss using standard automated perimetry (SAP) and short wavelength automated perimetry (SWAP)", *American Journal of Opthalmology*, Volume 134, Pages 177-185, 2002] and the somewhat similar scheme published by the Advanced Glaucoma Intervention Study (AIGS) Group ["The Advanced Glaucoma Intervention Study (AGIS): 1. Study design and methods and baseline characteristics of study patients", *Control Clinical Trials*, Volume 15, Pages 299-325, 1994].

Both the SAFE and AIGS methods pool clusters of HFA visual field points. This suggests that overall larger test regions, corresponding to the size and shape of the SAFE and AIGS pooling regions, may provide an additional advantage in the analysis of the visual field.

The Frequency Doubling Technology (FDT) perimeter, and the newer Matrix perimeter, both use test stimuli about the size of those pooling regions, about 10 degrees square, however the FDT test regions do not overlap in space, and the stimuli have sharp edges [see for example U.S. Pat. Nos. 5,065,767 and 5,912,723, each to Maddess].

It has been recognized by the inventors that by using a greater number of individual stimuli and positioning them in the visual field so that they would overlap in space (if the stimuli were presented simultaneously although this does not occur in practice except for multifocal methods of stimulus presentation where occasional overlap can be allowed) then not only could aliasing effects be minimized, but the processes of overlapping would mean that one of the large stimuli, of potentially the optimum size, would more often be presented centred on a region of damage within the visual field. Whilst U.S. Pat. Nos. 5,065,767 and 5,912,723 both indicate the benefits of testing with large stimuli but require the stimuli to exhibit the spatial frequency doubling illusion and do not disclose or suggest the use of overlapping stimuli to more correctly identify the location of patches of visual insensitivity, and guard against aliasing.

One form of perimetry, known as High-Pass Resolution perimetry (HPR), can include stimuli that overlap in space where ring-shaped stimuli of different sizes are presented centred on each visual field location of the HPR sample grid. The task in this method is to find the minimum stimulus size that is visible at each location where, in principle, larger ring stimuli could overlap. This overlap, however, would not reduce the effects of aliasing since each of the HPR ring targets contains only high spatial frequencies and thus would transmit to the measured field the high spatial frequencies contained in the visual field leading to aliasing.

By contrast, the stimuli described herein contain only lower spatial frequencies than the sampling grid can reconstruct.

Figure 11A:
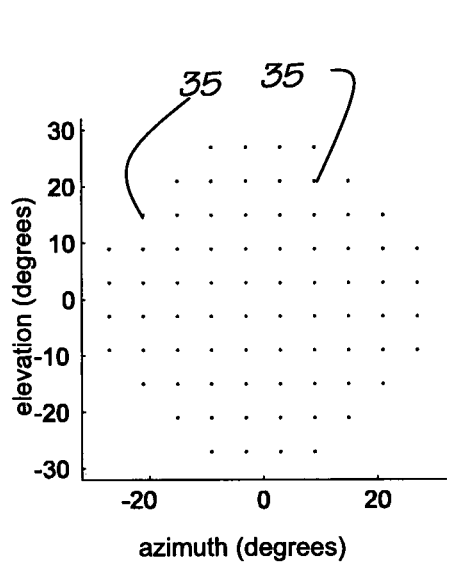
FIG. 11A shows a HFA 30-2 test pattern with a 6 degree sampling grid.

FIGS. 10A to 10C show an example overlapping spatial stimuli in accordance with the methods described herein that may be presented on a 6 degree grid of visual field locations similar to those in the HFA 30-2 test pattern. The grid of the centres of the 30-2 test locations is shown in FIG. 11A, the small circles approximating the size of standard HFA stimuli. The 24-2 pattern described above represents a subset of those test points on the same grid.

The stimulus example of FIGS. 10A to 10C show an example of an overlapping stimulus. In particular, FIG. 10A is a grey-scale plot showing the relative amplitude of stimulus patch 70 as a function of visual field position relative to the centre of the stimulus patch 70; FIG. 10B is a contour plot of the stimulus of FIG. 10A with iso-amplitude contours 72 at 20% intervals; and FIG. 10C shows many transects 74 through the stimulus patch 70 where amplitude is described as contrast. The transects 74 are indicative of the profile of the stimuli 70. Note that in this example, the stimulus 70 is large enough, i.e. greater than 6 degrees full-width-half-maximum (FWHM) 71) to create substantial overlap between adjacent stimulated regions on the 6 degree grid. Also, the edges 73 and or corners 75 of the profile of stimuli 70 are smoothly varying (i.e. sufficiently smooth or blurred). The degree to which the individual stimuli 70 are smoothly varying is chosen so as not to transmit higher spatial frequencies in the visual field that could otherwise form aliasing effects that could distort the shape of the measured visual field. The use of sufficiently smooth or blurred individual stimuli has been found to have the significant advantage that the subject does not need to be well refracted (that is, the subject under test may require refractive correction) when being tested. That is, incorrect, insufficient or even no refractive correction does not significantly affect the results of the assessment of the subject's visual field.

The smoothness of the stimulus is adequate if the Fourier transform of the stimulus does not itself contain frequencies higher than the Nyquist rate defined by the sampling grid. The edges 73 of the example stimulus in FIG. 10A appear blurred as they contain little high spatial frequency content. This particular type of stimulus can thus be referred to as a blurred stimulus. Persons skilled in the art will appreciate that the stimulus patches 70 could be of alternative sizes and shapes depending on the particular grid size or test pattern desired, and also that the roll-off off the edges 73 of the test patch 70 could be of an alternate form, provided that the edges do not introduce high frequency spatial Fourier components, to achieve the desired reduction in aliasing effects and other advantages of these type of stimulus as described above.

An additional advantageous feature of these overlapping, low spatial frequency stimuli is that that individual stimulus patches do not contain any high spatial frequency components and therefore their image contrast will not be diminished by refractive errors of several dioptres of either spherical of cylinder correction. That is, subjects/patients undergoing visual assessment with the burred overlapping stimuli described herein who have an incorrect spectacle (or other refractory vision aid eg. contact lenses) correction would see the stimuli 70 no differently than subjects with perfectly corrected vision. This has the significant advantage that for any given subject, providing their sensory nervous system was normal, the subject's visual assessment test results will be unchanged regardless of whether their vision correction is correct or not. Thus, less care can be taken to achieve good refraction when testing subjects with these large, blurred edged, stimuli.

Figure 11B:
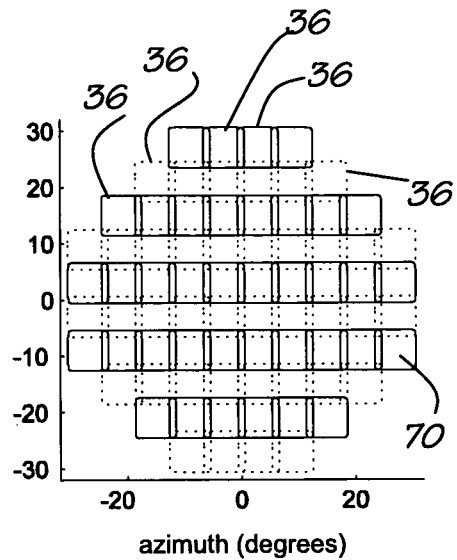
FIG. 11B is a schematic representation of the 50% contour lines of the stimuli of FIG. 10A arrayed in the HFA 30-2 test pattern of FIG. 11A showing the spatial overlap of the stimuli if they were to be presented simultaneously.
Figure 11C:
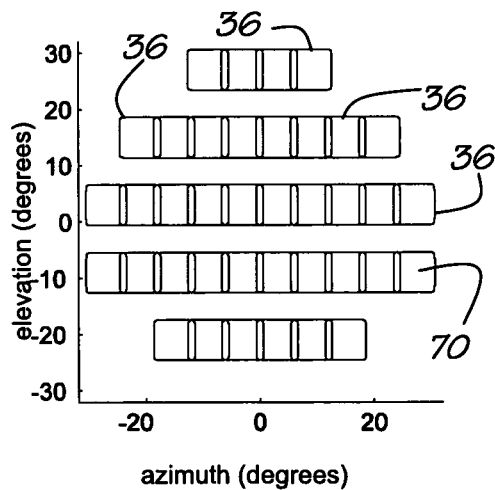
FIGS. 11C and 11D show respectively half the stimuli of FIG. 11B permitting the overlapping contours to be more clearly seen.
Figure 11D:
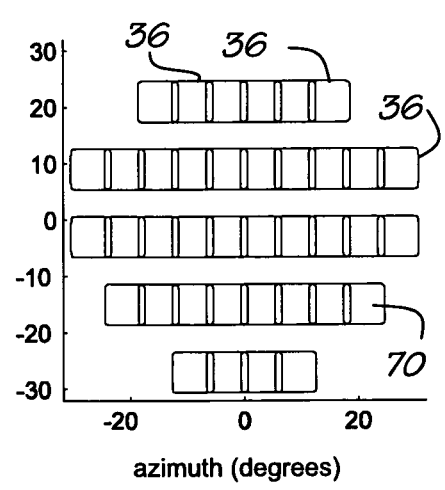
Figure 12:
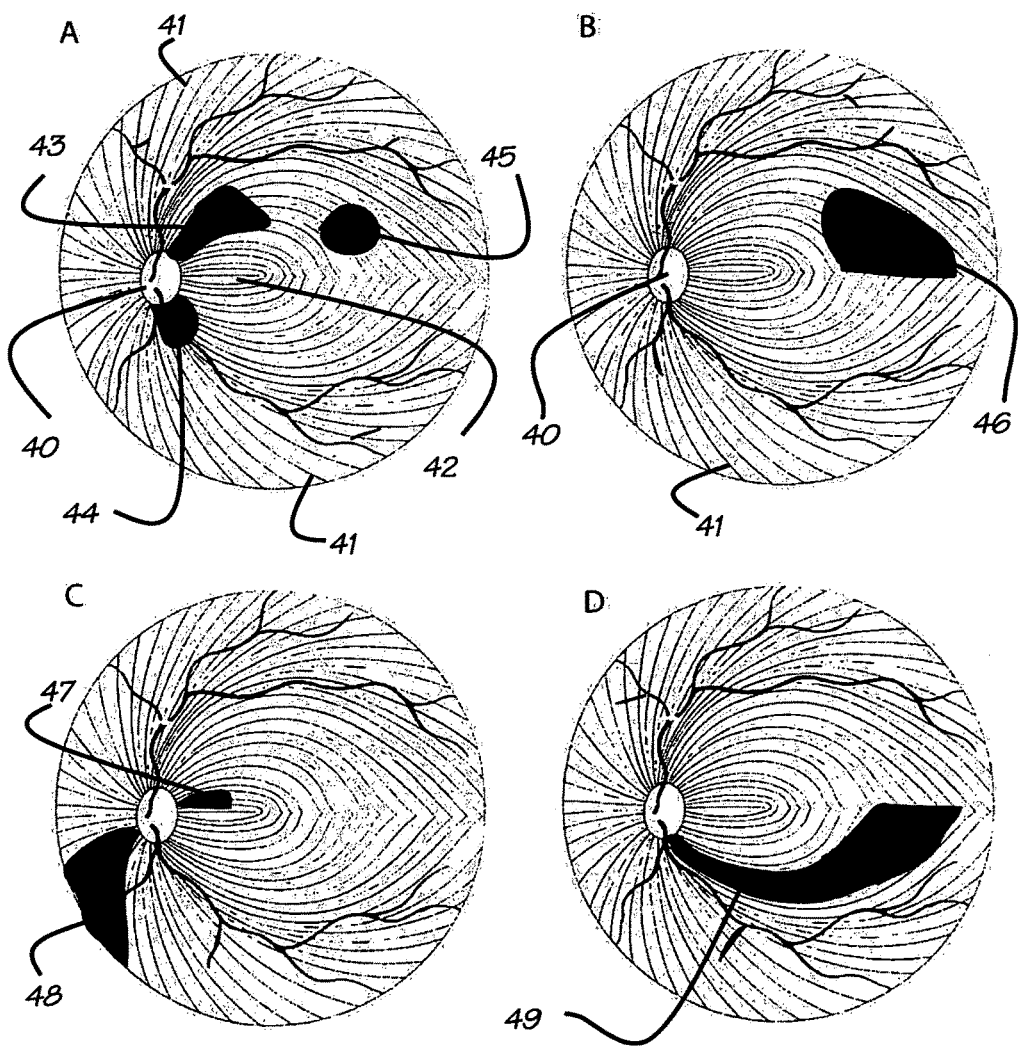
FIGS. 12A to 12D are schematic representations of a retina displaying the paths of the retinal ganglion cells across the retina to the optic nerve head or disc, and their possible influence on the shape of visual field sensitivity changes in response to damage to parts of the optic disc.
Figure 13A:
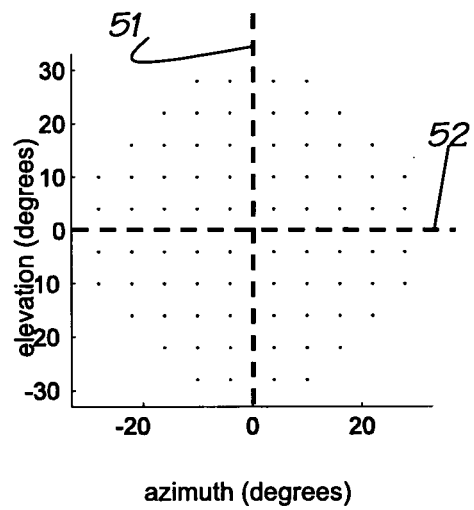
FIGS. 13A to 13D show a schematic representation of a stimulus ensemble similar to that of FIGS. 11A to 11D using the stimulus of FIG. 10A where the sampling grid has been adjusted so that the stimuli do not overlap the horizontal and vertical meridians of the visual field.
Figure 13B:
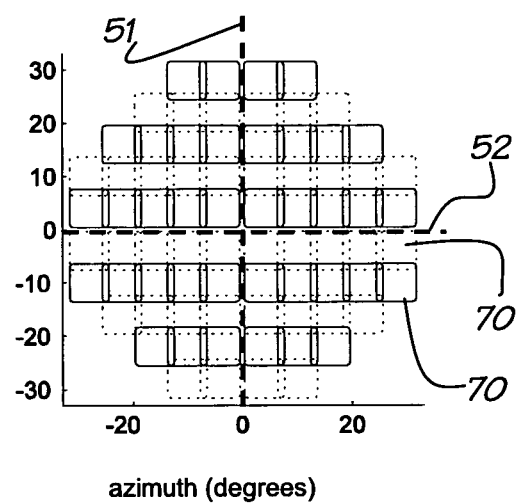
Figure 13C:
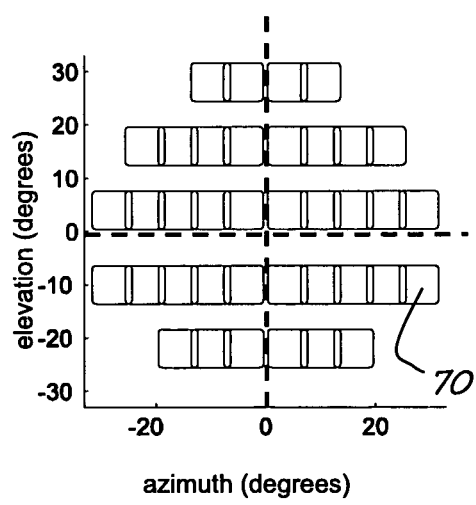
Figure 13D:
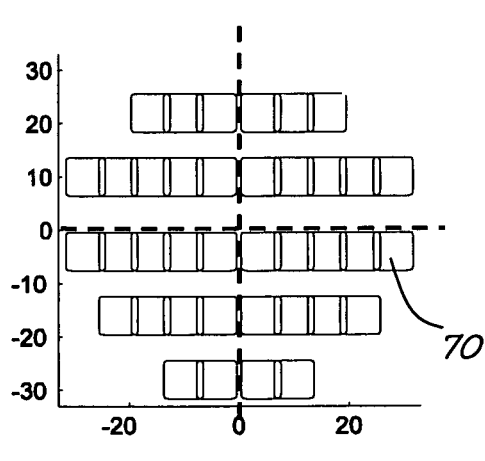

FIG. 11A shows an example visual test field with grid locations 35 at which a suitable stimulus is able to be presented to the visual field of a subject. FIGS. 11B to D show an example of overlapping stimulus patches (as per patches 70 of FIG. 10A) for an assessment of a subject's visual field in accordance with the above described methods. The contours 36 represent the 50% amplitude (FWHM) of the stimulus 70. FIG. 11B shows all the 50% contours 36 but with half drawn in dotted lines to permit the overlapping between adjacent stimuli to be more clearly visualized. FIGS. 11C and 11D each show half the patches of FIG. 11B, again permitting the overlapping contours to be more clearly seen. In use in an actual perimetry test, the stimuli 70 would either be presented one at a time at a particular grid location 35, or if two or more stimuli 70 are to be presented simultaneously, the grid locations 35 of the simultaneous stimuli would preferentially be non-adjacent grid locations such that no two stimuli overlap in space at the same time in any one test presentation (however, it is recognised that in some arrangements with a multifocal method the stimuli may be overlapping at some points in the stimulus sequences). As is typical for perimeters, the stimuli are presented one at a time and the positions of successively presented stimuli would be randomized across the grid of possible presentation locations (i.e. grid locations 35 of FIG. 11A). Alternatively the stimuli could be presented in a multifocal arrangement where the multifocal method would permit several stimuli to be shown concurrently on any of a sequence of presentations, but where the temporal sequences controlling the appearance of a stimulus at any one grid location are sufficiently statistically independent as to permit responses to each region to be estimated from records of nervous system responses to the ensemble of stimuli.

FIGS. 12A to 12D illustrates important features of the retinal ganglion cell anatomy. The 4 panels FIGS. 12A to 12D are each diagrammatic representations of the posterior retina as seen thorough the pupil by a fundus camera, a form of microscope for inspecting the interior of the eye. The optic nerve head 40 is depicted as the small vertically elongated oval to the left of each panel. The many thin arcing lines 41 connecting to the optic nerve head 40 to each part of the retina represent the possible paths of the retinal ganglion cell axons (also known sometimes as the raphe). The fovea 42 is located at the focus of the arcs just left of centre of each panel particularly the paths 41 along which the retinal ganglion cell axons travel to the optic nerve head 40 (also known as the optic disc). The large black patches 43 to 49 represent patches of the retina showing decreased sensitivity to visual stimuli. Of particular interest is that retinal ganglion cells from the superior retina send their axons to the superior optic discs and vice versa for the inferior retina. This the result of this is that, any process that causes damage at or near the optic disc 40, as can occur in glaucoma, can translate into arc-like damaged sectors (eg. patches 43 or 49 of FIGS. 12A, C, D) or triangular sectors (eg. patch 48 of FIG. 12C) of altered visual sensitivity. Another common feature is that these patches of altered sensitivity can respect the horizontal meridian (see for example damaged patches 46 or 49 of FIGS. 12B and D respectively) creating a fairly sharp horizontal border resulting in a so called step of sensitivity as illustrated by the inserts 20 and 30 of FIGS. 2 and 3 respectively. Neurological problems, such as strokes in the occipital visual cortex, often lead to changes in visual sensitivity that respect the vertical meridian. For these reasons it may make sense not to have stimuli that overlap across the horizontal and vertical meridians. This is a common feature of perimeters and can be seen in the 30-2 test grid for example (FIG. 10A). To achieve this with while stimuli using larger overlapping stimuli it would be sensible to move the stimuli 70 slightly away from these borders 51 and 52 as illustrated in FIG. 13.

Figure 14A:
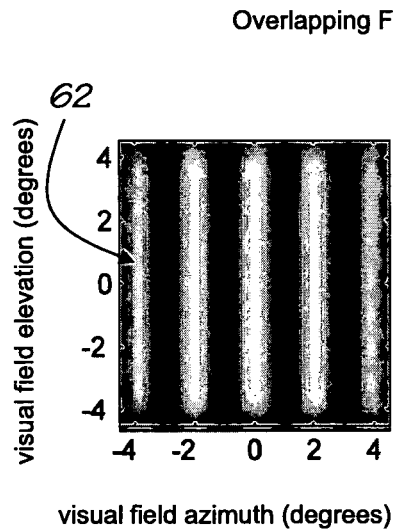
FIGS. 14A to 14D shows an example of a FDT N-30 stimulus ensemble modified to have overlapping stimuli, the stimulus contours being representative of the outer boundaries of the stimuli, the stimuli do not overlap with the horizontal and vertical meridians of the visual field.

A similar arrangement to that shown in FIGS. 11A to 11D may be envisaged for an overlapping stimulus version of the popular N-30 test pattern of the FDT perimeter. FIG. 14A for example illustrates a possible arrangement where the illustrated stripe pattern 62 represents a spatial frequency doubled pattern. Spatial frequency doubling occurs when the stimulus contain the conjunction of high temporal and low spatial frequencies. This includes stimuli which rapidly appear and then disappear in less than about 200 ms, or which drift rapidly across the visual field, as well as the contrast reversing method used in the FDT. An alternative is to use stimuli that produce the visual sensation of higher than doubled spatial frequencies which can occur for certain combinations of spatio-temporal conditions.

While the stimulus illustrated in FIG. 10A is approximately the same size as the FDT stimuli, it differs from those stimuli by having smoothed edges. The smoothing has been achieved in this example by multiplying the frequency doubled pattern with an envelope similar to that of that of FIG. 10A. Again, this further improves the tolerance of the stimulation method to mis-refraction (i.e. wrong or inadequate visual refractive correction in a particular subject) and the effects of aliasing of the high spatial frequencies found in the sharp edges of the standard FDT stimuli. For smaller stimuli, as used for example in the Matrix perimeter 24-2 test pattern, but with the same or similar spatial frequency to stripe pattern 62 illustrated in FIG. 14A, the smooth edges of the stimuli has an even more beneficial effect since for smaller stimuli the edge forms a proportionately larger part of the stimulus. This will also effect the sensitivity measurements obtained if the subjects attend more to the sharp edges than the spatial frequency doubling stimulus which itself contains only low spatial frequencies. If subjects attend to the high spatial frequency content of the edges, this would make the obtained responses more biased to those high spatial frequencies rather than the low spatial frequencies that produce frequency doubling, thus reducing the benefits of frequency doubling stimuli [see U.S. Pat. Nos. 5,065,767 and 5,912,723, each to Maddess].

Stimuli can appear to have higher than their actual spatial frequency content, from one to several times the actual stimulus spatial frequency, by virtue of a preponderance of low spatial frequency content, generally below 1 cycles per degree (cpd) except at near the fovea where spatial frequencies as high as 4 cpd may be used, coupled with rapid contrast reversal, rapid onset and offset, or rapid translation across the visual field within a region of the visual field, any of those temporal modulations corresponding to having the bulk of their power in the range 10 to 30 Hz.

Figure 14B:
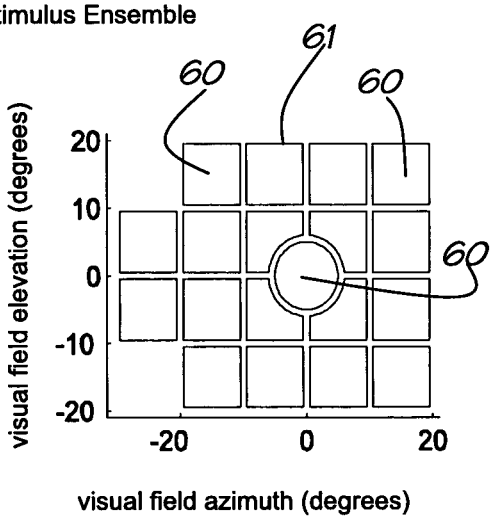
Figure 14C:
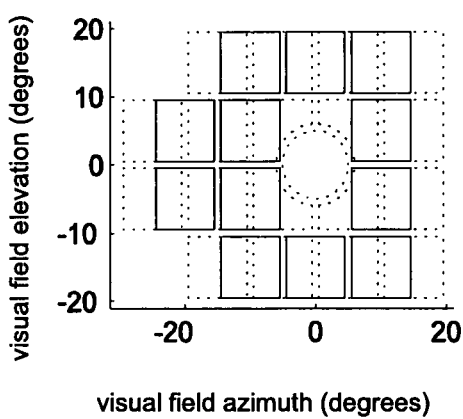
Figure 14D:
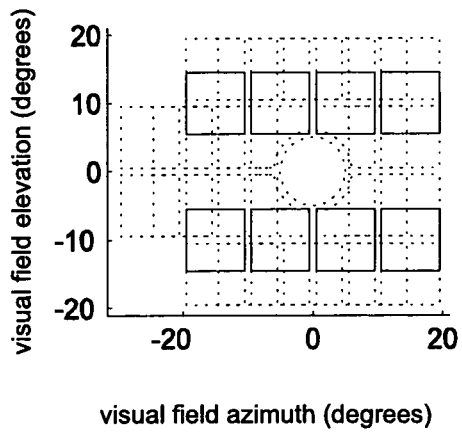

FIG. 14B illustrates the standard FDT N-30 grid of stimuli 60 for the right eye which could be of the frequency doubling type 62 (as seen in FIG. 14A). Unlike FIGS. 11 and 13, the stimulus contours 61 here represent the absolute boundaries of the stimuli rather than the 50% stimulus level of previous figures. FIGS. 14C and 14D show successive addition of overlapping stimuli 60 (where some of the stimuli 60 are depicted with a dotted outline for clarity). It will be recognised that the exact number of overlapping stimuli, their size, and regions and the overall extent of the visual field regions sampled may be altered without detracting from the methods described herein of overlapping, blurred stimuli. The actual implementation of such a test could either be behavioural or multifocal.

Polar Co-ordinate Representation

FIG. 12C shows a small arc-like patch 47 of altered sensitivity protruding towards the fovea. Given the discussion above on the relatively higher density of retinal ganglion cells in the foveal region this physically small patch may correspond to many more cells being damaged than in larger patches in peripheral regions of the retina. Therefore, the method of determination of the correct stimulus size needs to be carefully designed with regard to the density of ganglion cells in various parts of the retina. As pointed out above, the number of retinal ganglion cells is greatly magnified in the human fovea. This magnification is substantially mirrored in the visual cortex and so stimuli that have optimal sizes for detecting patchy retinal changes of sensitivity for a given retinal eccentricity will be optimal for detecting cortical changes of sensitivity. To a good approximation, the retinal cell density changes that occur with eccentricity are quite radially symmetric about the fovea. There are some small deviations from radial symmetry that could be optimized for, but for the purposes of illustration they have not been considered in the present discussion [for further information refer to C. Curcio and Allen K A, "Topography of ganglion cells in human retina", *Journal of Comparative Neurology*, Volume 300, Pages 5-25, 1990].

Considering initially a rectilinear system, the spatial autocorrelation function of visual fields showing patchy alterations may be computed to find the average, shift invariant, size of the patches. This approach, however, has limited utility in a substantially polar system such as the retina, or retinotopic visual brain areas. Therefore, if the visual field data obtained in some sampling grid defined on horizontal (h) and vertical (v) space, V(h,v), is transformed into a polar representation defined in terms of radius from the fovea (r) and polar angle about the fovea ($\theta$), V(r,$\theta$), and then the autocorrelation or some similar measure may be computed in the new polar representation to clearly identify regions of altered sensitivity. Using such a polar transformation, the resulting functions are found to have coordinates where unit areas are related to a fixed number of retinal cells per unit area in the transformed space. That is a particular patch in this space could thus correspond to some unit number of cells. It is believed that the use of polar representation in order to quantify field properties in this manner, and the corresponding advantages that can be obtained from this representation as will be discussed below, has not yet been realised by skilled persons in the art for visual field assessment. Furthermore, optimizations of the initial polar representation are available where the dimensions of the transformed visual fields might be some nonlinear functions, f(x) or g(x), of true visual field radius and polar angle, e.g. V($\rho,\psi$) where $\rho$=f(r) and $\psi$=g($\theta$) are also possible. For example, nonlinear transformations might be a better match to retinal ganglion cell densities in some part or parts of the retina. For the purposes of illustration, the following discussion has been limited to the linear case, however it will be appreciated that nonlinear polar representations are encompassed in the methods disclosed herein.

FIG. 15A shows data on the sensitivity of points in a visual field 90 obtained with the HFA 24-2 test pattern. Here, relative sensitivity in each region 91 of the visual field 90 is indicated by grey level: dark corresponding to low sensitivity (i.e. impaired sensitivity) and bright to high sensitivity. The sensitivity data for each point in the visual field 90 is represented as checks 91 presented against a black background. The size of the checks 91 does not indicate the size of the stimuli that were used to obtain the data. In this case the stimuli were the very small Goldmann size III stimulus presented spatially at the centre of each of the check shown. The standard quadrants, one to four, of rectilinear space are denoted by the notations Q1 to Q4 surrounding the plot. The black check 80 at −15 degrees azimuth just above 0 degrees elevation corresponds to the normal blind spot produced by the visually insensitive optic disc 40. This visual field plot represents an example of a V(h,v) function described above. It can be seen from FIG. 15A that this visual field shows a generalized loss of sensitivity that declines radially from fixation. This type of loss is common in glaucoma and is well detected by large stimuli. FIG. 15B shows the same data as that in FIG. 15A, however, it has been transformed into polar coordinates defined in terms of radius from the fovea (r) and polar angle about the fovea ($\theta$), and thus represents an example of a V(r,$\theta$) function as described above such that reductions in sensitivity of the visual field as a function of radius (FIG. 15A) appear as a linear gradient of reduced sensitivity in the polar representation (FIG. 15B). Triplets of rows (82, 84, 86 and 88) are marked by Q1 to Q4 and correspond to the quadrants of the FIG. 15A. Quadrant 1 82 is reproduced at the bottom of FIG. 15B to permit steps of sensitivity present at the boundary of quadrants 1 and 4 (Q1 and Q4) to be readily observed (for example as seen in damage features 46 or 49 of FIG. 12). Notice that in the polar representation, the foveal portion of the field within a 3 degree azimuthal/elevation radius (i.e. column 81 of FIG. 15B) is greatly expanded, but which is in line with the greater number of retinal sensory cells there, and the consequent emphasis on central scotomas in visual field classification. The normal blind spot corresponds to the black check 80 just below the central Q2 row.

The general decline of sensitivity with increasing radial eccentricity, left to right through column 81, 83, 85 and 87 in FIG. 15B, is clear. Computing the autocorrelation function of this visual field representation would be meaningful because, as indicated above, distance here from the fovea in this polar representation better equates to retinal cell number.

FIG. 16A shows an example of a visual field 100 that is quite seriously damaged by glaucoma. The arc 101 of residual peripheral sensitivity in quadrant 2 is seen as a vertical extension of sensitivity 102 in the upper part of the 21 degree column 87 of FIG. 16B. The step in sensitivity across the horizontal meridian is seen clearly as a step 103 across the quadrant 1 to quadrant 4 boundary. The arc of sensitivity loss 105 in quadrant 2 maps to a dark vertical rectangle 106 in quadrant 2. The loss almost all of quadrant 1 (in region 107) translates to a large horizontal rectangle 108 consisting of the top 2 rows of FIG. 15B.

FIG. 17A shows a further example of a visual field 110 from a glaucoma patient displaying a small arc-shaped, or arcuate, scotoma 111 below the fovea. In the polar representation of FIG. 15B, this arc 111 translates to a column 112 of loss in FIG. 16B at the bottom of the 3 degree column centred on 240 degrees polar angle. FIG. 17 shows a further example still of the visual field 115 from a glaucoma patient displaying a slightly more eccentric arcuate scotoma 116 that translates into a vertical rectangle 117 in the 9 degree column centred on about 210 degrees polar angle.

Overall, it can be seen that the polar transformation of the visual field has several advantages, in particular:

The relative magnification of cell numbers near the fovea is catered for. This then permits calculation of measures such as the mean autocorrelation length of scotomas in a cell number centric fashion.

Common features of retinal damage such as arc, sector and radially expressed losses translate into rectangles or linear gradients parallel to the carinal directions which are readily identified in the polar representation.

Features such as steps across the horizontal and vertical meridians are preserved.

Taken together, this information suggests that not only can these polar representations be used to choose optimum stimulus size, in terms of polar coordinates, but furthermore, the polar domain is readily adapted to the application of algorithms designed to recognise such damage since common features are rendered into a rectilinear representation. Indeed this suggests a more general method for data from a variety of perimeters, obtained on a number of sample grids, to be transformed into a standard polar representation before quantitative comparison.

Figure 23A:
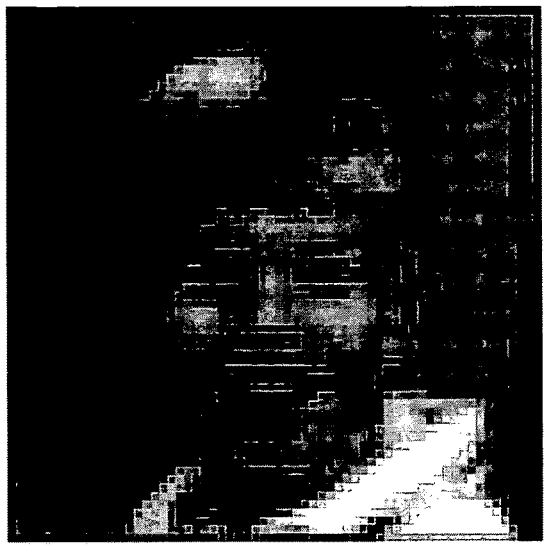
FIGS. 23A to 23D depict the effect of using median filters of various sizes and aspect ratios on an image matrix (FIG. 23A) having relatively few pixels.

Among the algorithms designed to recognise damage or other deviations from typical behaviour that could be implemented, such as those mentioned above, the autocorrelation or similar measure may be computed in the new polar representation to clearly identify regions of altered sensitivity, would be various forms of spatial filtering. These might include linear methods such as convolution with some operator or operator, or nonlinear methods such as median filters of other similar "edge preserving" filters. Examples of these methods and their potential benefits are illustrated in FIGS. 23 to 25 below and the associated Table.

Figure 19A:
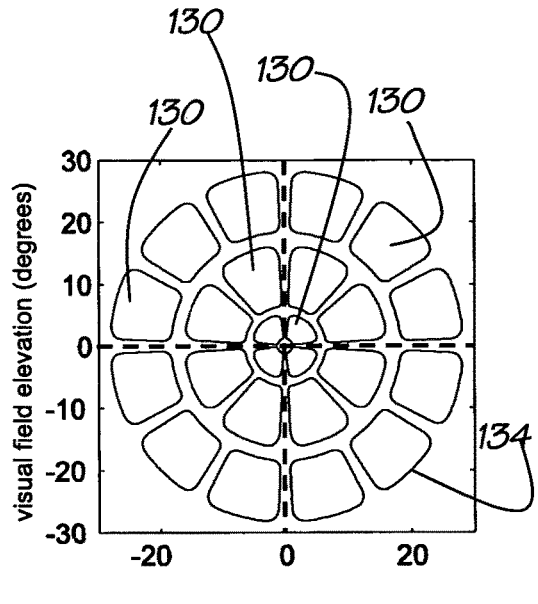
FIGS. 19A and 19B each show a respective half of an ensemble of large stimuli with blurred edges arranged in a O30-44 grid which respect the horizontal and vertical meridians of the visual field and showing an increase in the size of the stimuli with increasing with radius.
Figure 19B:
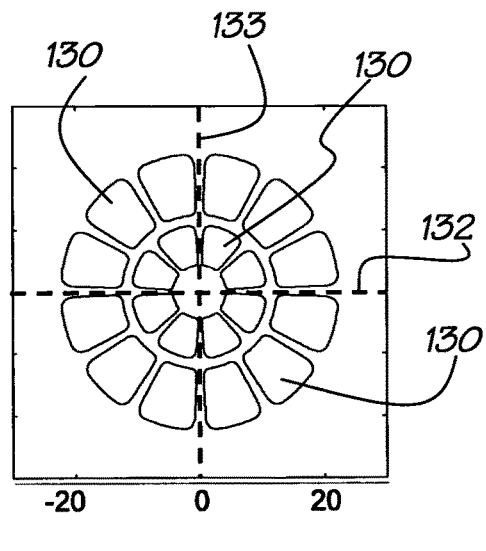
Figure 19C:
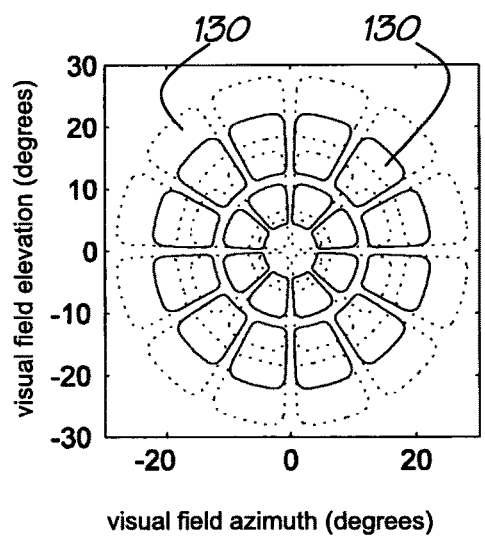
FIG. 19C shows the stimuli of FIGS. 19A and 19B showing the substantial spatial overlapping of adjacent stimuli if they were to be presented simultaneously.
Figure 19D:
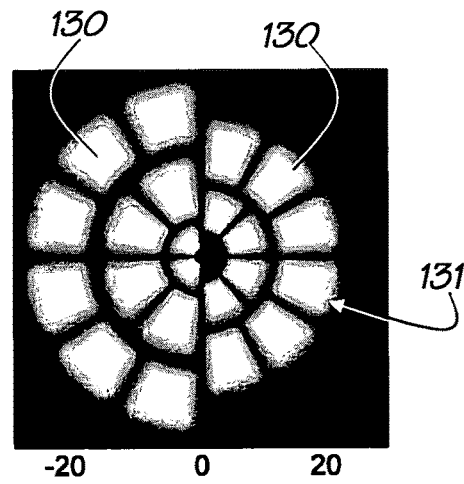
FIG. 19D shows a image of the polar stimulus ensemble of FIG. 19C where the left half of the image shows the left half of the stimuli of FIG. 19A and the right half of the image shows the right half of the stimuli of FIG. 19B.

FIGS. 19A to 19D illustrate an ensemble of perimetric stimuli that incorporate all the features outlined above. The individual stimuli 130 are large and have smoothly declining, blurred edges 131 to eliminate the effects of aliasing. The stimuli 130 have a radial layout with regions sizes that are roughly equal in area in a polar domain, thus each of the individual stimuli 130 stimulates roughly the same number of retinal cells or cells in thalamic or cortical visual areas. The ensemble of stimuli respect (i.e. do not intersect or cross) the horizontal and vertical meridians 132 and 133 of the visual field so that stimuli do not overlap across the boundaries possibly obscuring meridional steps in visual sensitivity. More specifically, FIG. 19A shows contours 134 for 24 of the stimuli 130 at their 50% level. FIG. 19B shows the same contours for the remaining 20 stimuli 130. FIG. 19C shows the contours of all 44 individual stimuli 130 (with half of the stimuli shown in dotted outline for clarity) to show the spatially overlapping nature (if they were to appear simultaneously) of the stimuli as used in assessment of the visual field according to the methods described herein. FIG. 19D shows the blurred appearance of the stimuli 130 (only half of the stimuli are presented on each side of the vertical meridian for clarity) as they appear in the display monitor of the visual field assessment apparatus described below.

It is worth noting that the optimum size may be partly determined by signal to noise ratio where the range over which spatial correlations are significantly similar is determined both by the autocorrelation function and the signal to noise ratio. In short, if the true autocorrelation function of the spatial signal being measured is known, but the particular sample is noisy, then by taking an average over a slightly larger area, the correlated features in the particular sample can be determined. For visual field testing, particularly in the case where a retina is more damaged and so perhaps providing a noisier signal, this implies that even larger stimuli may be required. The ability to determine the optimum stimulus size in this manner has significant advantages, particularly for example in the improvement of test repeatability.

The previous discussion has been related to the stimulation of and assessment of the visual field of a subject, however, the methods described above are equally applicable to the assessment of any sensory field. Examples of other sensory fields which are applicable to treatment with large overlapping stimuli as outlined above include the tactile sensory field on the skin, or the audio-visual field described by binaural differences in the arrival time of sounds and the corresponding azimuth angle on the horizon of the visual field where the sound source is located. Several examples of such poly-sensory fields are given in International Patent Publication No. WO 2005/051193 to Maddess & James. The sensory field can also be generalized to more dimensions that two, including for example the combination of the tactile and visual fields as occurs when an observer sees a tactile stimulus on their skin. The implication here is that the benefits of overlapping stimuli would be useful in these other sensory domains.

Apparatus

Figure 20A:
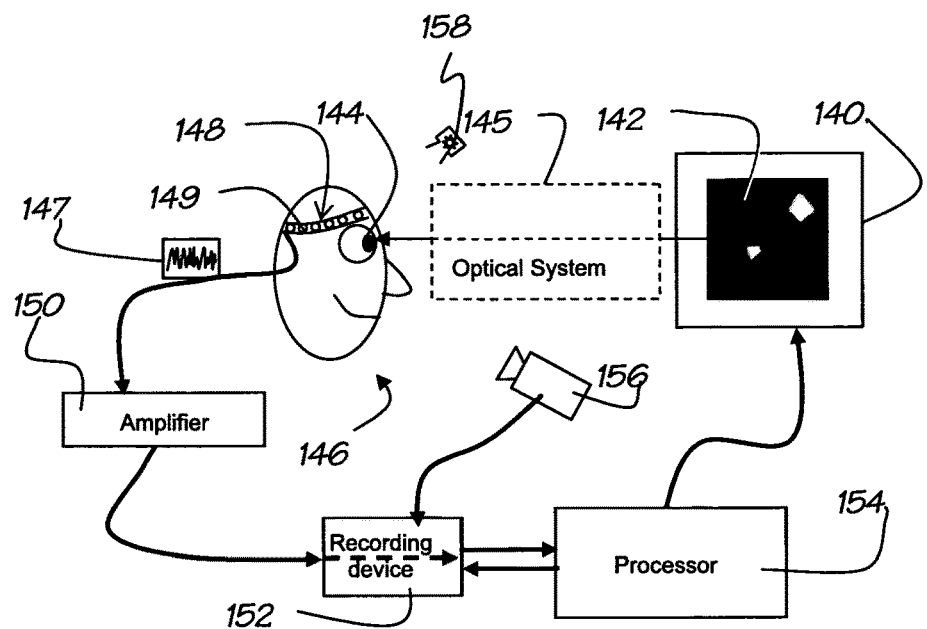
FIG. 20A is a schematic diagram indicating components of an apparatus and system for visual field assessment.
Figure 20B:
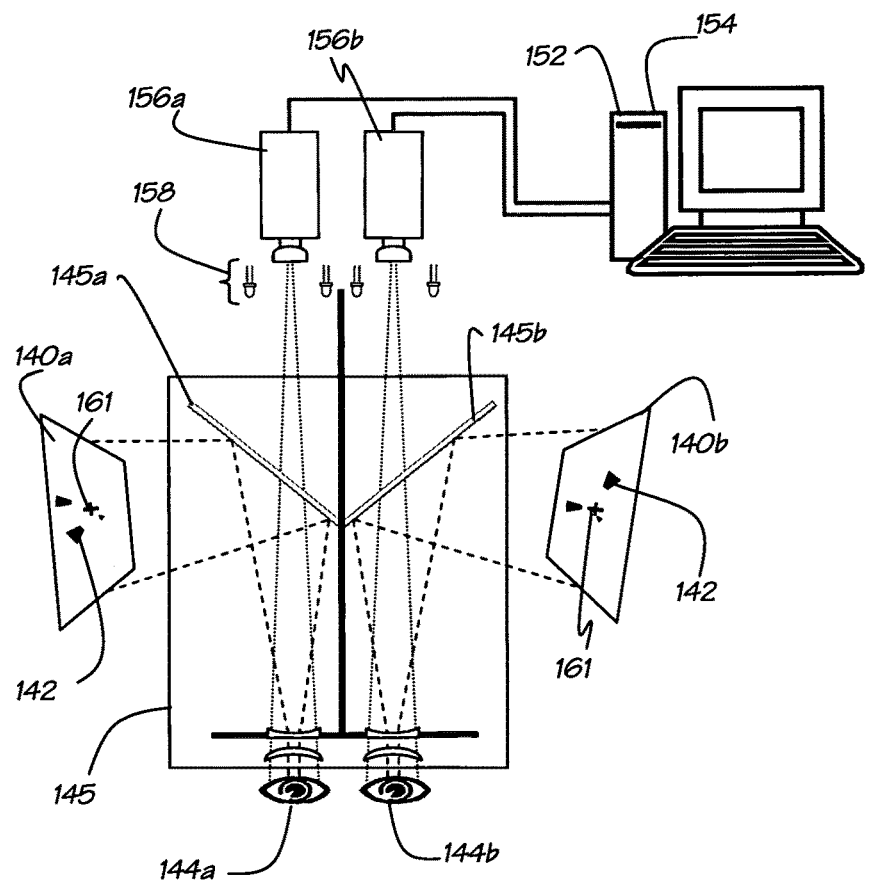
FIG. 20B is a schematic diagram of a stereoscopic arrangement of an exemplary apparatus and system for visual field assessment.

A schematic of the basic system components forming an embodiment of the apparatus of the present invention is shown in FIG. 20A. The major components are a display device 140 (e.g. a CRT, LCD, plasma, LED, organic LED (OLED) or similar display screen) presenting visual stimuli 142 to one or both eyes 144 of a subject 146. The stimuli are optionally presented to the subject via a suitable optical system 145 for example to enable magnification control of the image to simulate a distant object. A sensor 148 for detecting cortical neural responses from the subject in response to the stimuli 142 is provided such as for example electrodes 149 (e.g. standard gold cup electrodes placed on the scalp to record the evoked potentials) attached to the subject's head. Responses 147 from the sensor 148 are amplified in an amplifier 150 and visual evoked electrical potential corresponding to the responses are recorded in a recorder 152. A computation and control device such as a processor unit 154 is also provided for computing estimated coefficients of the linear and non-linear weighting functions characterising the responses 147 to the stimuli 142, and also for controlling the presentation of the stimuli 142 on the visual display 140. Additional monitors and or detection/recording devices may also optionally be used as required such as a camera or cameras 156 for monitoring of the subject's pupil dilation for example, and an additional illumination source or sources 158, such as an infrared light source, may be provided to illuminate the subject's eyes to assist in the monitoring of, for example, the subject's eye position, gaze direction, or pupil dilation (see for example the apparatus of FIG. 20B described below).

In use for the visual field assessment of a subject 146 test stimuli images 142 for each subject were presented on a visual display at a desired mean rate of presentation. Since the stimuli 142 are presented on a visual display, it is common to refer to the sequence of pictures presented as a sequence of frames presented at a particular frame rate, e.g. 75 frames per second although the frame rate may vary widely between 1/20 of a frame per second to 1000 frames per second (it will be appreciated by the skilled addressee that it is not the actual frame rate which is significant, but the mean rate of presentation of the stimuli at each region/location). In some arrangements, the same stimuli may remain appear for a duration lasting a plurality of frames. In the example described below, the frame rate was 30 images per second per eye and video records of the pupil size were recorded at 60 frames per second. In other arrangements the images may have temporally modulated brightness or other sensory dimension while they are on for several frames. In the multifocal case, the appearance of the stimuli at each location is governed by pseudorandom sequences that are statistically sufficiently independent so as to permit linear and or nonlinear weighting functions to be estimated that characterise the response of each part of the sensory field stimulated. These sequences will typically deliver the stimuli at a rate that this not directly related to the frame rate but instead would have mean presentation rates of between about 1/20 per second per region and 10 per second per region, and typically between 0.2 per second per region and 5 per second per region. The duration of presentation of the stimuli should be much shorter that the mean interval for each region rendering them temporally sparse. It will be appreciated, however, that different rates of delivery at each region or mixtures of rates for each region are also possible. The layout of the plurality of stimulus regions is shown in FIG. 19C. Other examples stimulus arrangements would be those depicted FIG. 11B, FIG. 13B, and FIGS. 14B, 14C and 14D.

During the test, subjects were asked to fixate a spot (for example cross-mark 161 of FIG. 20B) presented at the centre of the plurality of visual stimulus regions. Persons skilled in the art will recognise that other techniques maintaining fixation, such as monitoring the subject's eye and/or gaze position, may be employed, and the position of the test stimuli on the display screen 140 altered to in response to changes in the subject's gaze position. In the present example, responses of the visual nervous system were recorded by video records from camera 156 of the subject's pupil diameters obtained under infrared illumination of the eyes from light source 158 and recorded by the recording device 152. The recording device may be incorporated into the processor, and the processing done in real time, in which case data from the detector sensor may not need to be recorded or stored until post-processing. Alternatively electrical evoked potentials 147 could be obtained from the sensor 148. It will be appreciated that the presently described apparatus for visual assessment may be substituted, particularly the sensor for detecting the neuronal responses evoked by the stimuli, is not restrictive and various aspects of the apparatus may be substituted as would be appreciated by the skilled addressee.

In this regard, persons of skill in the art will recognise that evoked neuronal responses may be detected by alternate techniques other than by measuring electrical potentials such as by detecting and/or recording changes in magnetic, or electromagnetic radiation, or acoustic signals, responses of the pupil or movements of the eyes. In the case of electromagnetic or acoustic monitoring sensor, the electromagnetic or acoustic signals are either passive signals emitted by the brain, or the effects of scattering absorption, refraction or reflection of electromagnetic or acoustic energy transmitted towards or through the brain, could also be employed. The use of two or more of these detection techniques in some combination is also not excluded.

EXAMPLES

Example 1

The present example describes the visual field assessment of a subject according the above described methods using a multifocal visual field architecture wherein objective records of neural responses of both the subject's retinas were obtained by simultaneously recording the responses from each of the subject's two pupils in response to a dichoptic stimulation using blurred, smooth-edged and overlapping stimuli. Dichoptic stimulation is independent stimulation of the visual fields of the two eyes.

A separate O30-44 stimulus ensemble was presented to each eye using a stereoscopic arrangement of the apparatus as depicted in FIG. 20A that directs images of 2 separate liquid crystal (LCD) displays 140a and 140b, one to each of the subjects eyes 144a and 144b. The real-time diameter of each pupil was recorded and monitored using separate video cameras 156a and 156b under infrared illumination from IR LEDs 158 (a plurality of such LEDs shown). The processor 154 controlling the presentation of the stimuli on the two displays 140a and 140b, collecting and storing the recorded data from the video cameras, and processing the recorded data is depicted in the present case as a computer system. The optical system of the apparatus 145 in the present case comprises two dichroic "cold mirrors" 160a and 160b for directing the image from the displays 140a and 140b to the subjects eyes 144a and 144b. The cold mirrors are configured such that they are highly reflective for the wavelengths (colour) of the stimuli presented on the displays, and simultaneously highly transmissive at the wavelength of the IR LEDs for recording the real-time diameter of each pupil from the IR light reflected back from the pupil of the subject's eyes. The background illumination level of each LCD was 10 $cd \cdot m^{-2}$. When a given stimulus region was active the centre of the stimulus region had a brightness of 290 $cd \cdot m^{-2}$. Rather than being white, the individual stimuli used in the present example (as depicted in FIG. 19D) were yellow in colour on the display screens of the apparatus. In some arrangements the background of the display may also be yellow. Yellow stimuli reduce the possible effects of brunescence of the subject's ocular lenses, which absorbs blue light, where the degree of brunescence depends on roughly on the subject's lifetime exposure to UV light, and thus the effect of brunescence increases with the subject's age. Macular pigments also absorb blue light and their optical density varies from person to person. Therefore, it has been found to be advantageous to use stimuli which have no blue colour components, for example yellow.

The longer wavelengths of the yellow stimuli are also relatively less scattered by small media opacities within the eye. Overall, yellow stimuli therefore produce less variable illumination of the retina of different subjects than white light illumination. This is not a limiting design and it will be recognized that other colours of light, or combinations of colours, may have other advantages.

The pseudorandom modulation of the 88 stimulus regions was designed to ensure that the stimuli had the properties of temporal and spatial sparseness [see for example U.S. Pat. No. 6,315,414, U.S. Pat. No. 7,006,863, and International Patent Publication No. WO 2005/051193, all to Maddess and James]. Temporal sparseness is the property that the stimuli are presented transiently between longer intervals of null stimulation, preferably with presentation rates between 0.25 and 4 presentations per region per second. Accordingly, when activated, a stimulus region remained at 290 cd·m$^{-2}$ for only 33 ms and the mean presentation rate was 1 stimulus per second per region. Spatial sparseness is the property of ensuring that, if a given region is active, then regions adjacent to that region are not to be simultaneously active. Temporally and spatially sparse stimuli increase the signal to noise ratio of the recorded responses. The total duration of the test stimulus ensembles was 4 minutes, but where this was broken up into 8 test segments of 30 seconds duration.

The study group in the present example contained 43 normal subjects and 44 subjects with glaucoma yielding 174 eyes. The visual damage of the glaucoma patients was categorised into mild, moderate and severely damaged visual fields. There were about equal numbers of the three visual field types amongst the glaucoma subjects. In addition to the O30-44 stimuli with large, blurred-edged, overlapping stimuli as shown in FIG. 19C, the subjects were also tested in the same recording session with a T30-24 multifocal test ensemble using the same apparatus. The T30-24 pattern is a subset of the O30-44 pattern and is illustrated by FIG. 19A and the left half of FIG. 19D. With the exception of the lack of overlapping stimuli the T30-24 were otherwise identical to the O30-44 stimuli. A minimum of two minutes rest time was given between the two test types, which were given in randomized order across subjects.

Figure 21A:
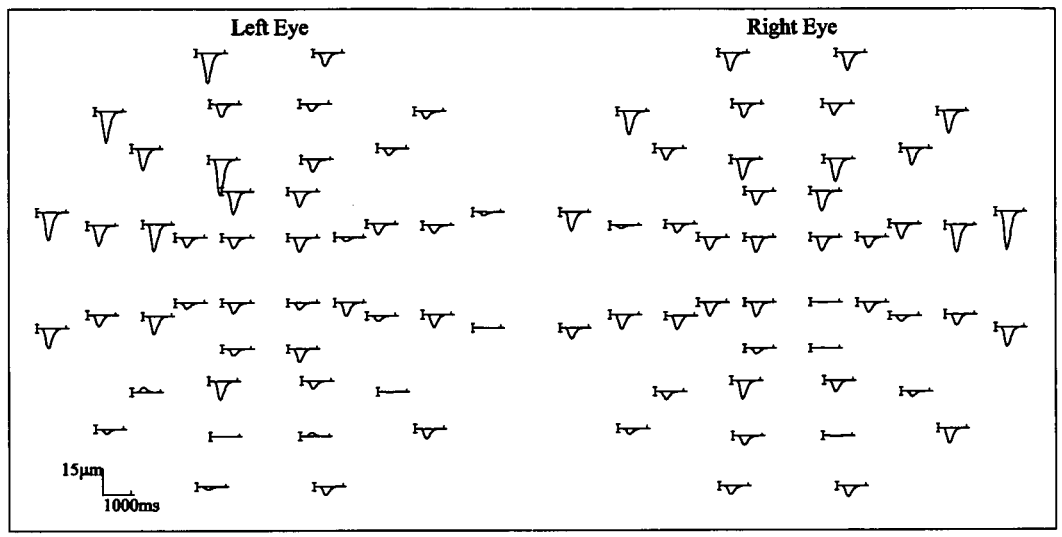
FIGS. 21A and 21B respectively show responses of the left and right pupils of a subject to a multifocal polar visual field stimulus with the O30-44 arrangement of FIG. 19C displaying a pair of responses to each visual field location from the left and right pupils.
Figure 21B:
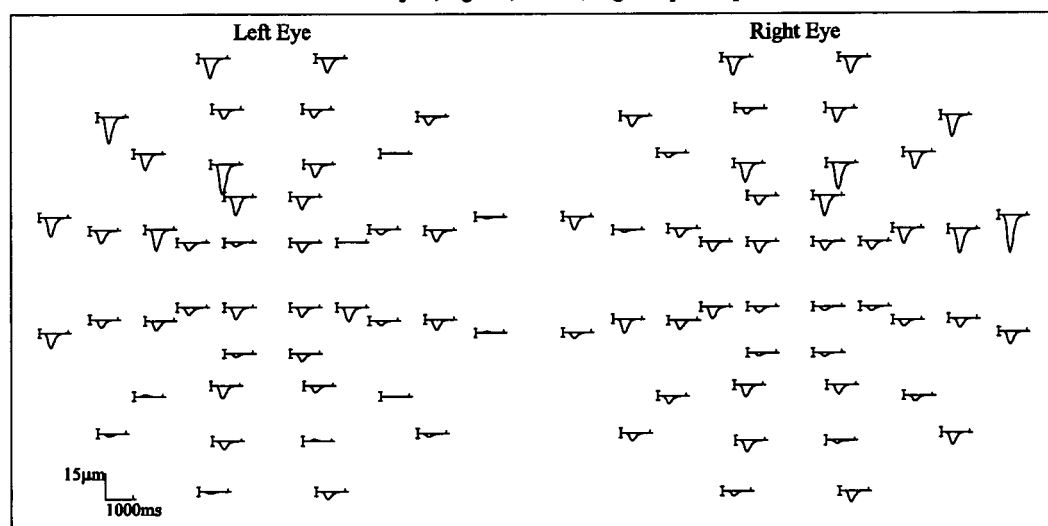

FIGS. 21A and 21B respectively show the responses from a subject's left and right pupils, and so too the retinas from which the pupillary responses are derived, to the multifocal visual field stimulus. Note that there is one response for each pupil and stimulus region roughly plotted at the location of the O33-40 stimuli in the visual field. The stimulating system concurrently displayed two independent multifocal versions of the O33-40 stimulus ensemble, one ensemble being shown to each eye. The result is a pair of responses to each visual field location, the pair of responses originating from the left and right pupils that provide independent estimates of the response of both eyes.

Figure 22:
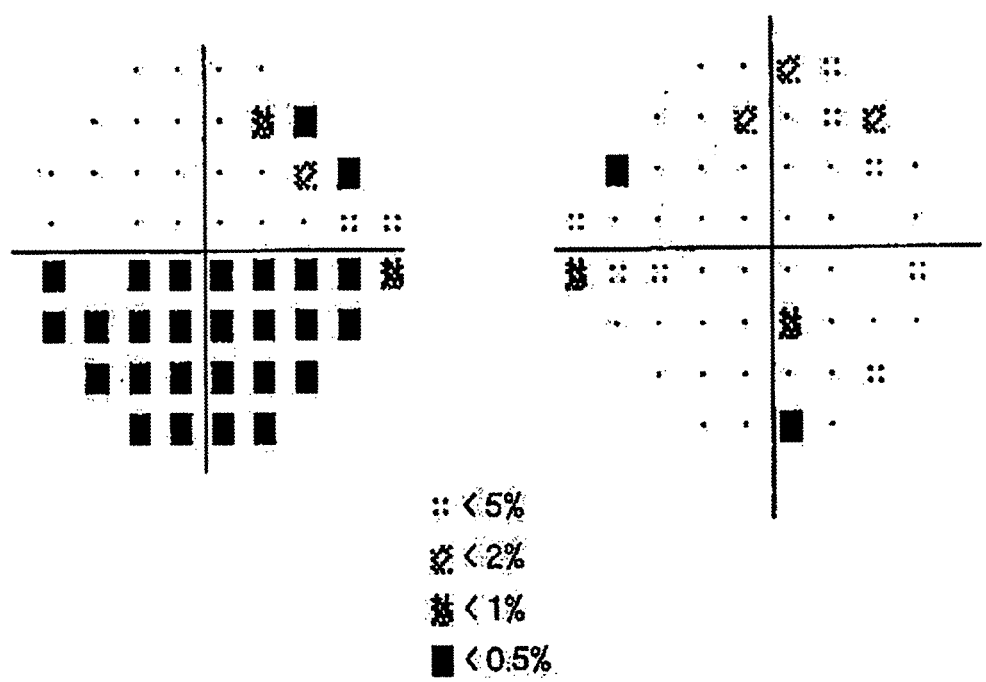
FIG. 22 shows the probability of normal function as a function of retinal location as measured by a HFA 24-2 test for comparison with the polar overlapping visual field stimulus method described herein.

FIG. 22 shows the probability of normal function for the same subject as in FIG. 21 as measured by the HFA 24-2 test. The correspondence between the probability of normal performance and grey level is given in the legend. By comparing responses from the overlapping stimuli O33-40 test with the non-overlapping stimuli HFA 24-2 test in the left and right eyes, it can be seen that the left inferior field in FIG. 21 has smaller responses than in the corresponding part of the right visual field as the HFA results would suggest.

To quantify the ability of the two test methods to characterize changes in sensitivity with visual fields, formed receiver operator characteristic (ROC) plots were generated (not shown) of the sensitivity for recognising the visual field of a glaucoma subject against the false positive rate for misidentifying the visual field of a normal subject. This is a well recognized method for characterising the ability of a system to measure signal in the presence of noise. In an ROC plot, perfect performance has an area under the curve in the plot of 1 (or 100% probability of an accurate measurement). Chance performance equates to an area under the ROC plot of 0.5 (50% probability of an accurate measurement). Table 1 below shows the results from the ROC plots for the T30-24 and O30-44 by visual field category. Discrimination

TABLE 1

Percentage Area under ROC Plots for Diagnosis of Glaucoma

| | Glaucoma vs. Normals Discrimination power (%-area under ROC plot) | |
| --- | --- | --- |
| Test | O30-44 (Overlapping stimuli) | T30-24 (Non-overlapping stimuli) |
| Mild | 70.9% | 67.0% |
| Moderate | 71.1% | 68.2% |
| Severe | 80.2% | 80.4% |

The rows of Table 1 indicate visual field category and the two right columns the results in terms of percent area under the ROC plots. While the two overlapped and non-overlapped methods perform essentially at the same level, about 80.3%, for severe fields, the O30-44 method performed markedly better for mild and moderate fields indicating good underlying sensitivity for identifying relatively undamaged glaucomatous fields.

In all cases the ROC plots were formed based on scores that were a linear combination of the area of the pupillary response waveforms, as shown in FIG. 21, and their time to peak. The score was derived from a standard linear discriminant function based on those two variables. For a given subject, these variables were sorted from smallest to largest and the N smallest scores for the normal and glaucoma fields were the input to the discriminant and ROC analyses. This was repeated for various values of N and the ROC values for the best performing N is shown in the Table 1 above. This is a straightforward process that is quite applicable to mild visual field defects where the damage is likely to be more diffusely distributed. In severe fields the areas of damage tend to be clustered and so are amenable to various forms of two dimensional analysis of clusters of damage that would be expected to increase the ROC areas for severe fields.

As mentioned above, a particular advantage of transformation to a rectilinear polar domain is the possibility of performing such operations as filtering to emphasise damage that can expressed as rectilinear blocks in polar coordinates such as those illustrated in FIGS. 15B, 16B, 17B and 18B (for example, block 102 of FIG. 16B). By recognizing that the features of damage being sought can be rectilinear in the polar domain, it is possible to perform spatial filtering of the visual field data with operators of a particular size and aspect ratio. The size of the spatial filter operator may be identified by, for example. Autocorrelation analysis of the visual field data in a rectilinear polar domain. In other arrangements, elongated filter operators may also be appropriate since they mimic the size and shape of the rectangular blocks (for example, block 102 of FIG. 16B, block 112 of FIG. 17B, block 117 of FIG. 18B) representing damage to the raphe of nerve fibres 41.

Figure 23B:
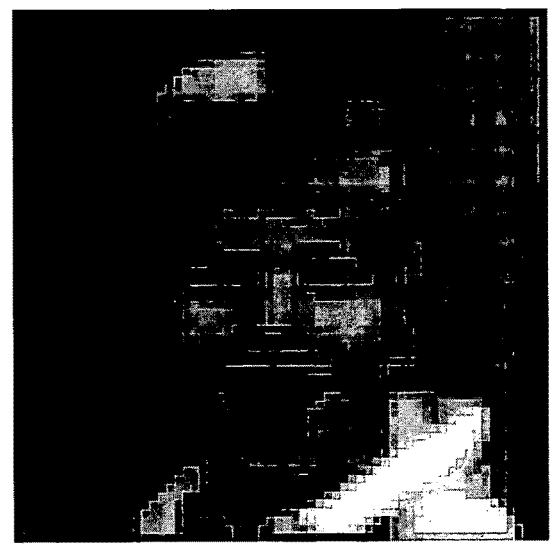
Figure 23C:
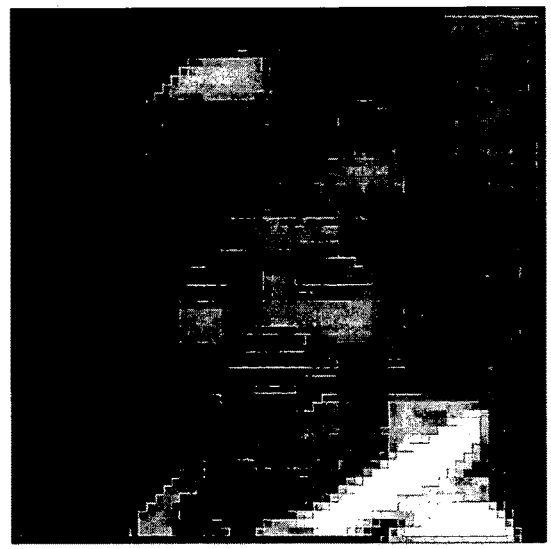
Figure 23D:
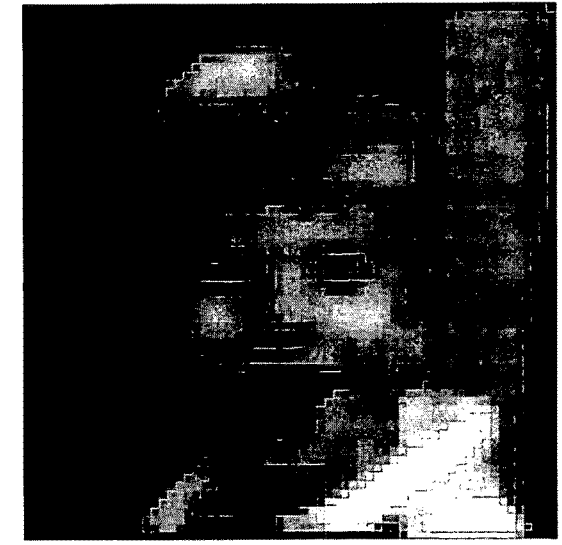
Figure 24:
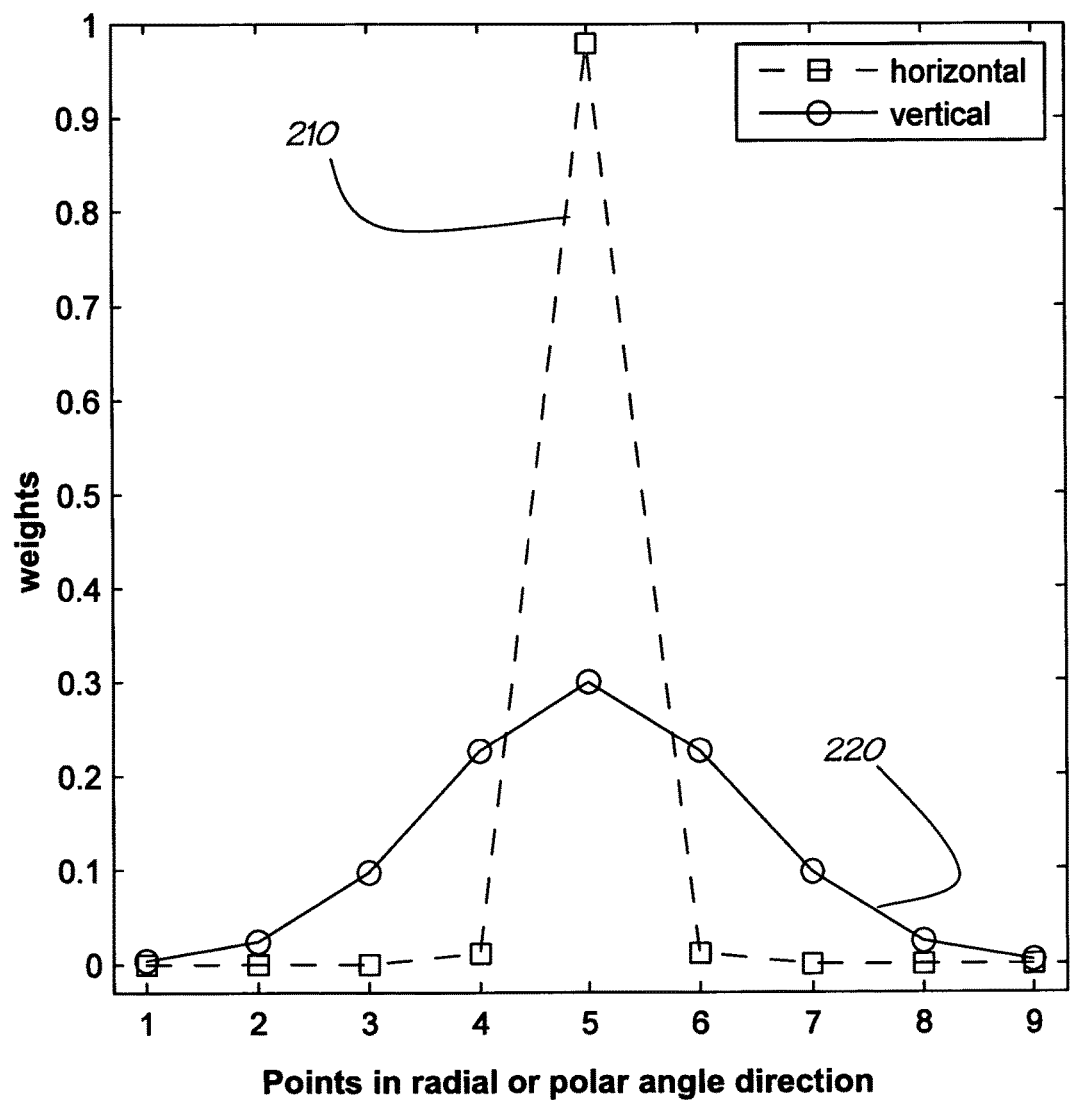
FIG. 24 is a representation of two exemplary operators for linear filtering of an image for assessment of a subject's visual sensory field.

Examples of the effect of using median filters of various sizes and aspect ratios on an image matrix (FIG. 23A) having relatively few pixels (such as those shown in FIGS. 15B, 16B, 17B, and 18B) are shown in FIG. 23B to FIG. 23D. A median filter works by recursive application of a small window of fixed dimensions in which the window is moved across the image point-wise, and the median value of pixels falling under the window is computed and then placed back into the image. Median filters are commonly used to remove extreme values from images. FIG. 23A shows the original image. FIG. 23B shows the effect of using a median filter where the moving window was 3 pixels high and 1 pixel wide. FIG. 23C shows the effect of using a median filter where the moving window was 1 pixels high and 3 pixels wide. These filters tend to preserve vertical or horizontal features of the image while generally smoothing along their long axis. FIG. 23D shows the effect of using a median filter where the moving window was 3 pixels high and 3 pixels wide.

Similar forms of linear filtering can also be done with the convolution of appropriate operators with the image. A convenient way to do this that is similar to the examples given for median filters (FIGS. 23B to 23D) is to convolve the image representing the sensory field data with different operators in the vertical and horizontal directions. In the case of the polar representation of visual field data, different operators would be used along the radius and polar-angle directions. Examples of two such operators are given in FIG. 24. Both operators 210 and 220 are one dimensional Gaussian probability density functions. The narrow function operator 210 is intended to be convolved vertically across the image, and the wider function operator 220 convolved with the image horizontally. Notice that the half heights of the operators 210 and 220 respectively correspond to about 1 or 3 pixels, and so are comparable in size to the 3×1 pixel median filter of the expel of FIG. 23B. The weights of both kernels are set so that the area underneath each of the operators 210 and 220, and therefore DC gain, is set to 1.

Figure 25A:
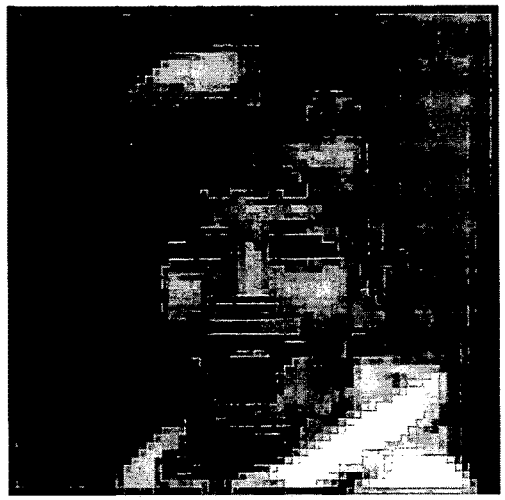
FIGS. 25A to 25D depict the effect of using the linear Gaussian filters of FIG. 24 in different combinations to produce two dimensional filters with varying sizes and aspect ratios on an image matrix (FIG. 25A) having relatively few pixels.
Figure 25B:
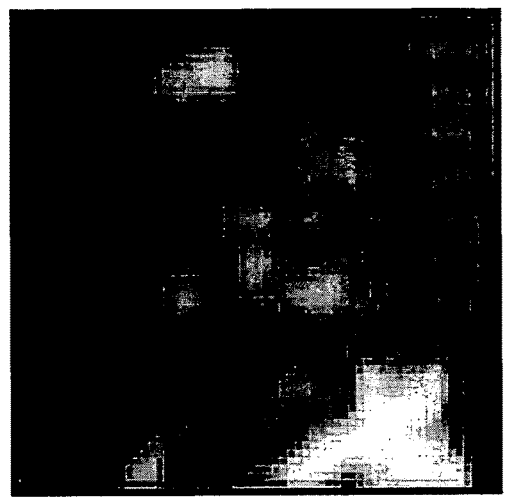
Figure 25C:
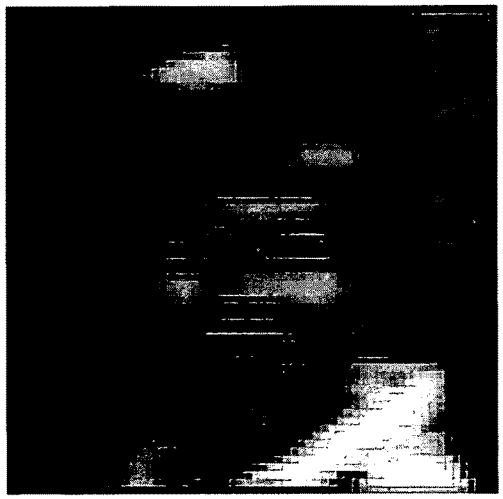
Figure 25D:
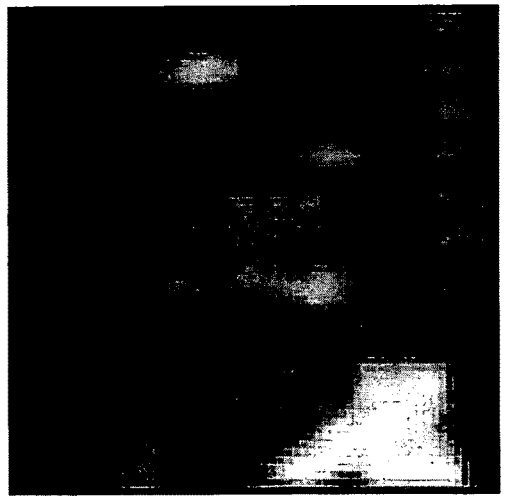

The effects of convolving the operators 210 and 220 of FIG. 24 with the same image of FIG. 23A is shown in FIGS. 25A to 25D. FIG. 25A shows the original image which is the same image in FIG. 23A. FIG. 25B shows the effect of using convolution with the operator 220 with half height 3 pixels in the vertical direction and high and the 1 pixel wide operator 210 in the horizontal direction. FIG. 23C shows the effect of swapping the vertical and horizontal filters. Again, these operations preserve vertical or horizontal features of the image while generally smoothing along their long axis. FIG. 25D shows the effect of using the broad 3 pixels wide operator 220 in both vertical and horizontal directions.

To examine the effect of these types of operations on the ability to identify changes to the visual field, visual field data from 62 normal subjects and 63 glaucoma patients was collected. The collection method was a multifocal presentation of a O30-44 stimulus with the spatial layout described above with respect to FIGS. 19A to 19D. Due to the large number of subjects in the sample, the visual fields of the subjects could be classified into categories of increasing damage. This was done using the mean defect classification technique, which determines the mean of the deviations from normal sensitivity across the visual field, as assessed by a Humphrey Field Analyser (HFA) perimeter. Mildly affected visual fields were said to have an HFA mean defect less than −6 dB of sensitivity reduction. Moderately affected visual fields had mean defects greater than −12 dB and less that −6 dB. Severely affected fields were classified as those visual fields recorded with mean defects greater than −12 dB.

Table 2 below shows results for diagnosing glaucoma expressed as percent area under ROC plots. The columns correspond to the sizes in pixels of the moving windows of median filters. The domain size in vertical and horizontal pixels is given at the top of each column. Several of the domain sizes are the same as those in FIG. 23A. The leftmost column (Labelled "No Filter") shows the results when no filtering is applied.

TABLE 2

Percentage Glaucoma Diagnosis using Median Filter

| | Glaucoma vs. Normal Discrimination (%-area under ROC plot) Filter Domain Size (vert × horiz. no. pixels) | | | | | | |
|---|---|---|---|---|---|---|---|
| | No Filter | 3 × 1 | 3 × 2 | 3 × 3 | 1 × 3 | 4 × 1 | 6 × 1 |
| All Cases | 71.7 | 70.8 | 68.5 | 67.3 | 69.1 | 69.1 | 66.9 |
| Mild Cases | 66.0 | 65.3 | 63.7 | 63.4 | 63.5 | 66.0 | 64.1 |
| Moderate Cases | 78.6 | 76.4 | 77.6 | 75.0 | 77.9 | 73.9 | 72.0 |
| Severe Cases | 93.7 | 94.4 | 92.4 | 89.0 | 94.9 | 90.2 | 88.5 |
| Moderate or Severe Cases | 85.4 | 83.9 | 83.1 | 79.9 | 84.2 | 81.2 | 79.3 |

Although the results for the filtered data are often slightly poorer than for no filtering it is clear that generally elongated filters perform better than more isotropic ones. Much the same results are observed for convolution in the vertical and horizontal directions using Gaussian operators such as operators 210 and 220 of FIG. 24. The noise removal may make the reported fields more reproducible with no major loss of diagnostic power as can be seen in Table 3 below.

TABLE 3

Percentage Glaucoma Diagnosis using Gaussian Linear Filters

| | Glaucoma vs. Normal Discrimination (%-area under ROC plot) Filter Domain Size (vert × horiz. no. pixels) | | | | | | |
|---|---|---|---|---|---|---|---|
| | No Filter | 3 × 1 | 3 × 2 | 3 × 3 | 1 × 3 | 4 × 1 | 6 × 1 |
| All Cases | 71.7 | 68.9 | 68.1 | 65.4 | 67.9 | 68.3 | 67.4 |
| Mild Cases | 66.0 | 64.7 | 65.0 | 62.4 | 63.6 | 64.6 | 64.3 |
| Moderate Cases | 78.6 | 73.2 | 71.6 | 69.4 | 75.1 | 71.8 | 70.3 |
| Severe Cases | 93.7 | 90.7 | 88.5 | 84.5 | 90.9 | 90.3 | 89.5 |
| Moderate or Severe Cases | 85.4 | 81.1 | 79.3 | 76.2 | 80.9 | 68.3 | 79.0 |

Generally the median filters performed better (Table 2) than the linear (Gaussian) filters for comparable filter dimensions (Table 3). It is also clear that very long filter windows perform worse that those of about 3 pixels long in the long direction. This illustrates the idea expressed above that a critical scale, and rectilinear shape of analysis window, enhances the ability to detect changes in the visual field. Clearly the example filtering operations demonstrated here are presented for illustrative purposes only and are not limiting. Many varied forms of filters and operators may be employed by the skilled address whilst remaining in the scope and spirit of the techniques illustrated above. For example, one or more linear filters may be used which may alternatively or in combination comprise running means or Gaussian windows. The one or more filters may be edge preserving filters. The edge preserving filters may be selected from one or more of median filters, forward-backward median filers [for example as described by S. H. Chung and R. A. Kennedy in their article entitled: "Forward-backward non-linear filtering technique for extracting small biological signals from noise", J. Neuroscience Methods, vol. 40, p 71-86 (1991)], or iterative nonlinear filters [for example as described in D. Harwood, et al "A new class of edge-preserving smoothing filters" Pattern Recognition Letters, vol. 6 p. 155-162 (1987)].

Example 2

The benefits of the overlap method are not restricted to glaucoma diagnosis. For example in a study of 29 normal subjects and 20 subjects with Age-related Macular Degeneration (AMD)

For the present example, the two types of stimuli presented to the subjects in the study were slightly different types of stimuli to those that were employed for the previous Example.

About half of the patient eyes had less severe dry AMD, and half more severe wet AMD, 4 eyes were clinically normal in appearance. The normal and patient groups were well matched for age and gender.

As in the examples above the stimuli either had 24 non-overlapping regions as per the stimuli described with reference to FIG. 19A above and described as T30-24 stimuli, or 44 regions that overlapped as shown in FIGS. 19C and 19D described as O30-44 stimuli above. The only difference between the stimuli used in the present example to that of Example 1 is that in both cases in the present example, both multifocal stimulus arrays were scaled down in size by a factor of 2. Each array of the present example therefore subtends a 15 degrees radius instead of 30 degrees, hence these stimulus layouts are referred to as T15-24 and O15-44 stimulus arrays. These stimuli were designed to characterise the more central defects of AMD.

As in the previous Example 1 above, the stimulus regions were yellow but had a maximum luminance when presented of 250 cd/m$^2$ on a background of 10 cd/m$^2$. The duration for which each of the individual stimuli was presented to the subject on the display of each stimulus on presentation was 33 ms. One further variant was also included which altered the mean interval of pseudo-randomly ordered presentations of the multifocal stimuli at each location to be either 1 or 4 seconds. Hence the four stimuli examined in all subjects were designated T15-24-1 and O15-44-1 for the faster stimuli presented at mean interval 1 s, and T15-24-4 and O15-44-4 for the slower 4 s mean interval stimuli. Here again the measure of diagnostic power was the percent area under ROC plots. The maximally obtained areas are shown in Table 4

TABLE 4

Percent area under ROC plots for diagnosis of AMD

Normal vs. AMD Discrimination (%-area under ROC plot)

| Test | O15-44-1 | O15-44-4 | T15-24-1 | T15-24-4 |
|---|---|---|---|---|
| N-worst | 85.7% | 84.8% | 67.8% | 76.7% |
| Asym | 95.9% | 94.8% | 88.1% | 88.4% |

The upper row (labelled N-worst) are the percentage areas under the ROC plot) obtained if the worst few regions within one eye are considered (recall from Example 1 above that an area of 100% represents perfect diagnostic performance and 50% chance performance). The lower row (Asym) records the percentage of diagnosed cases based on the difference between comparable regions in the left and right eyes of individual patients, and hence records between-eye asymmetries in the visual fields of each test subject. Asymmetries between the visual field of normal subjects are compared with asymmetries in the patients.

It is clear that, regardless of the presentation rate, or whether between-eye asymmetry was considered, the overlapping stimuli of the O15-44-1 and O15-44-4 tests outperformed the non-overlapping stimuli of the T15-24-1 and T15-24-4 tests. This demonstrates that the particular scale of the stimuli and the sampling grid should be matched to the task.

Example 3

In a further example of the use of overlapping stimuli for visual field assessment, the yellow T30-44 290 cd/m$^2$ described above were used in a study of 23 normal subjects and 23 patients with non-insulin depended diabetes melitis (NIDDM). Of the 23 patients with NIDDM, only one showed any obvious sign of diabetic retinopathy, and this subject displayed some microaneurisms. The normal and patient groups were well matched for age and gender.

Mean pupil size was not significantly different between the normal and NIDDM patient groups and mean pupils size did not carry any significant diagnostic power in the present study. This suggested that the pupils of the patients were not affected by diabetic neuropathy.

The diagnostic performance based on the N-worst regions (expressed as areas under ROC plots) for the 16 eyes from the 8 patients who had experienced NIDDIM for at least 10 years was 0.89%±0.06% (mean±SE) (based on difference from normal performance, asymmetries are differences between the eyes compared in normal subjects and patients). When between-eye asymmetries of normal and AMD subjects were considered ROC area was 0.97%±0.03% when between-eye asymmetry was considered.

Since non-overlapping stimuli were not examined in this study this example did not demonstrate a difference between overlapping and non-overlapping stimuli. Nevertheless the present example does demonstrate the utility of the method for studying changes to sensory field for situations other than glaucoma.

SUMMARY

In summary therefore of the methods disclosed above and the examples, it is demonstrated that if visual field contained variations in sensitivity across space that could not be represented by the coarse sampling grids used in conventional static automated perimeters, then this could lead to distortions in the shape of the measured field. The fact that these spatial frequencies do exist is verified in FIGS. 1 to 4. To solve this problem, test stimuli that would overlap in space if presented together are used in conjunction with the edges of the test stimuli being sufficiently smooth that they will not capture any of the distorting higher frequencies. Thus, the individual stimuli have reduced high spatial frequency content themselves and so have blurred edges. This is suitable for perimetry given that the appearance of such blurred stimuli will not change (that is, the contrast of the stimuli will not be demodulated) even if a person is misrefracted, potentially by several dioptres. The sufficiently smooth or blurred individual stimuli have the significant advantage that the subject may not be well refracted (that is, may have incorrect, insufficient or even no refractive correction) without significantly affecting the results of the test.

It is further shown to be advantageous that highly overlapped stimuli enable spatially translated versions of the stimulus to be more accurately aligned with areas of changed visual field sensitivity. This also captures the utility of stimuli that are quite large as suggested by the quite successful FDT perimeter stimuli and the size of the pooling regions demonstrated above to analyse HFA visual field data.

Further still, it is found that, although overlapped stimuli may have some advantages, stimuli that would not overlap with the horizontal and vertical meridians of the visual field have been demonstrated as having the ability to accurately detect transitional changes or damaged regions of the visual field.

Further, it is appreciated that the above considerations are applicable to any sensory space of any number of dimensions.

Still further again, it is found that the radial symmetry and central concentration of retinal cells towards the fovea implies that the search for optimally sized stimuli for each visual field location is better investigated not using the fields themselves, but fields transformed into a polar space. For much the same reason data obtained from a variety of perimeters might best be compared in such a polar space.

Finally, it has also been found that higher spatial frequencies than can be represented by the coarse sampling grids of standard perimeters highlights the prospect of using those frequencies in some way without increasing the density of the sampling. At least the power, if not the phase, of these super-Nyquist frequencies can be estimated if the sampling grids are suitably random.

It will thus be appreciated that the methods, apparatus & systems described and/or illustrated above at least substantially provide a improved assessment and quantification of the sensory fields field of human and animal subjects, particularly the visual fields of eyes.

The methods, apparatus & systems described herein, and/or shown in the drawings, are presented by way of example only and are not limiting as to the scope of the invention. Unless otherwise specifically stated, individual aspects and components of the methods, apparatus & systems may be modified, or may have been substituted therefore known equivalents, or as yet unknown substitutes such as may be developed in the future or such as may be found to be acceptable substitutes in the future. The methods, apparatus & systems may also be modified for a variety of applications while remaining within the scope and spirit of the claimed invention, since the range of potential applications is great, and since it is intended that the present methods, apparatus & systems be adaptable to many such variations.

The invention claimed is:

1. A method for assessing a function of a visual sensory field of a subject, the method comprising:
   obtaining a system comprising a processor and a sensor for use with the processor,
   the processor configured to present on a display or optical system visual stimuli over selected areas of the visual sensory field defined by sensory spatial dimensions defined in units of angle or length of the visual sensory field, the selected areas being centered at points on a sampling grid of the display or optical system wherein individual visual stimuli
   each spans a portion of the visual sensory field, and
   each is selectively presented in a distinct associated area, wherein
      the distinct associated area of at least one of said individual visual stimuli overlaps a portion less than all the distinct associated area of at least one other of said visual stimuli such that spatial aliasing of the visual stimuli of the sampling grid is minimized, and
      profiles of the visual stimuli are smoothly varying such that the individual visual stimuli comprise mainly spatial frequencies that are less than or equal to a highest spatial frequency that can be represented by the sampling grid, wherein the highest spatial frequency is a Nyquist sampling frequency defined by a density of the visual stimuli in the sampling grid,
   the sensor configured to detect responses in the subject's visual sensory field evoked by the stimuli and generate inputs representative of the responses;
   using the processor to present visual stimuli including the one and one other visual stimuli;
   using the sensor to detect responses in the subject's visual sensory field evoked by the visual stimuli including responses evoked by the one and the one other visual stimuli and generate the inputs representative of the responses evoked by at least the one and the one other visual stimuli,
   the processor configured so that the overlap of the distinct associated areas of the at least one and at least one other visual stimuli presented by the processor and smooth varying of the profiles of the visual stimuli presented by the processor avoid undersampling and reduce distorting effects of aliasing of high spatial frequency variations in visual function of the subject; and
   through the processor, processing the inputs to thereby estimate a functional response of the subject's visual sensory field at the selected areas using the detected responses.

2. The method as claimed in claim 1 wherein the sensory field has a horizontal meridional axis and a vertical meridional axis, and the visual stimuli presented by the processor do not overlap with either the vertical or horizontal meridional axes of the sensory field.

3. The method as claimed in claim 2 wherein the visual stimuli are presented by the processor to each span an area of the sensory field such that, in use, each visual stimulus stimulates equal numbers of sensory neurons in the sensory field.

4. The method as claimed in claim 1 wherein the sampling grid is presented in a polar representation coordinates of the polar representation being linear or nonlinear functions of radius and polar angle.

5. The method as claimed in claim 1 wherein the visual stimuli are presented by the processor so as to produce a perception of a spatially frequency doubled arrangement such that perceived spatial frequencies are between 30% lower than frequency doubled frequencies and 200% of the frequency doubled frequencies.

6. The method as claimed in claim 1 wherein the step of using the sensor to detect responses comprises using the sensor to detect responses in the subject's sensory field evoked by the visual stimuli by a method selected from the group consisting of:
   detecting electrical potentials;

detecting changes in magnetic or electromagnetic radiation;

detecting changes in acoustic signals;

detecting changes in the responses of the subject's pupil; and detecting changes in movements of the subject's eye, or a behavioral response of the subject.

7. The method as claimed in claim 1 wherein the step of using the processor to present visual stimuli comprises using the processor to present visual stimuli in a multifocal arrangement and the processing comprises the step of computing through the processor linear and/or nonlinear weighting functions that characterize the response of each stimulated portion of the sensory field stimulated by the visual stimuli.

8. The method as claimed in claim 7 wherein the step of using the processor to present visual stimuli comprises using the processor to concurrently present visual stimuli that are temporally sparsely presented, wherein temporally sparsely presented is the presentation of visual stimuli transiently between longer intervals of null stimulation.

9. The method as claimed in claim 7 wherein the step of using the processor to present visual stimuli comprises using the processor to concurrently present visual stimuli that are spatially sparsely presented, wherein spatially sparsely presented visual stimuli are presented such that if a given point on the sampling grid is active, the points on the sampling grid adjacent to the given point is not simultaneously active.

10. The method as claimed in claim 7 wherein the step of using the processor to present visual stimuli comprises using the processor to concurrently present visual stimuli that are temporally sparsely presented and spatially sparsely presented wherein temporally sparsely presented is the presentation of visual stimuli transiently between longer intervals of null stimulation and, wherein spatially sparsely presented visual stimuli are presented such that a given point on the sampling grid adjacent to an active point is not simultaneously active.

11. The method as claimed in claim 9 wherein the step of using the processor to present visual stimuli comprises using the processor to present two or more spatially sparse visual stimuli simultaneously.

12. The method as claimed in claim 1 wherein the step of using the processor to present visual stimuli comprises using the processor to present visual stimuli at locations on a multi-dimensional sampling grid.

13. The method as claimed in claim 1 wherein the step of using the processor to present visual stimuli comprises using the processor to present visual stimuli at locations on a regular sampling grid.

14. The method as claimed in claim 1 wherein the step of using the processor to present visual stimuli comprises using the processor to present visual stimuli at locations on an irregular sampling grid.

15. The method as claimed in claim 1 further comprising the steps of obtaining one or more filters having an aspect ratio of 3 to 1, the one or more filters being edge preserving filters, and enhancing generally elongated features within a polar representation of a space defined by sensory dimensions of the sensory field by operation of the one or more filters.

16. The method as claimed in claim 15 wherein the step of processing the inputs comprises transforming the detected responses to a rectilinear representation of the stimulated portions of the sensory field.

17. The method as claimed in claim 1 wherein the step of processing the inputs comprises transforming the detected responses to a polar representation of the stimulated portions of the sensory field.

18. The method as claimed in claim 1 wherein the sensory field under assessment is a plurality of dimensions, each dimension being one or two visual sensory fields of the subject.

19. The method as claimed in claim 1 wherein the step of using the processor to present visual stimuli comprises using the processor to present visual at least two stimuli and the sensory field under assessment is at least one visual sensory field of the subject encompassing a visual field sensitivity of one or both retinas of the subject.

20. The method as claimed in claim 19 comprising using the system to assess the visual sensory field of one or both retinas of the subject using a method for diagnosing a condition causing visual impairment.

21. The method as claimed in claim 20 wherein the condition is at least one of glaucoma, age-related macular degeneration, diabetic retinopathy, stroke, and multiple sclerosis.

22. An apparatus for assessing a function of a visual sensory field of a subject, the apparatus comprising:

a display or optical system controlled by a processor configured to present visual stimuli over selected areas of the visual sensory field, the selected areas being centered at points on a sampling grid of the display or optical system with each presented visual stimuli spanning a portion of the visual sensory field and presented in a distinct associated area, the distinct associated area of at least one of said individual visual stimuli overlapping a portion less than all the distinct associated area of at least one other of said visual stimuli such that spatial aliasing of the visual stimuli on the sampling grid is thereby minimized, wherein profiles of the visual stimuli are smoothly varying such that the individual visual stimuli comprise mainly spatial frequencies that are less than or equal to a highest spatial frequency that can be represented by the sampling grid, wherein the highest spatial frequency is a Nyquist sampling frequency defined by a density of the visual stimuli in the sampling grid, the processor configured so that the overlap of the distinct associated areas of the at least one and at least one other visual stimuli presented by the processor and smooth varying of the profiles of the visual stimuli presented by the processor avoid undersampling and reduce distorting effects of aliasing of high spatial frequency variations in visual function of the subject to thereby give an accurate identification of variation in the user's visual function across a measured visual field; and a sensor adapted to detect responses in the subject's visual sensory field evoked by the visual stimuli, said processor being operably connected to said sensor and to said display or optical system and configured to process the detected responses to estimate a functional response of the subject's visual sensory field at the selected locations using the detected responses.

23. The apparatus as claimed in claim 22 wherein the processor is configured so that each presented visual stimulus spans an area of the sensory field such that, in use, each visual stimulus stimulates equal numbers of sensory cells in the sensory field.

24. The apparatus as claimed in claim 22 wherein the apparatus is configured to present the sampling grid in a polar representation of a pace defined by sensory dimensions of the sensory field, coordinates of the polar representation being linear or nonlinear functions of radius and polar angle.

25. The apparatus as claimed in claim 22 further comprising one or more filters for enhancement of generally elongated features with the polar sampling grid, the one or more filters being edge preserving filters.

26. The apparatus as claimed in claim 22, the apparatus configured to compute linear and/or nonlinear weighting functions that characterize the response of each stimulated portion of the sensory field stimulated by the visual stimuli.

27. The apparatus as claimed in claim 22 wherein the apparatus is configured to assess a visual field sensitivity of one or both retinas of the subject and further comprises a display device selected from the group consisting of a CRT, LCD, plasma, LED, and OLED image display screen.

28. The apparatus as claimed in claim 22 wherein the sensor for detecting responses evoked by the visual stimuli is configured to detect neural or behavioral responses from the subject.

29. The apparatus as claimed in claim 22 further comprising a memory for recording the responses.

30. The apparatus claimed in claim 22 wherein the processor is configured to present visual stimuli so as to produce a perception of a spatially frequency doubled arrangement such that perceived spatial frequencies are between 30% lower than frequency doubled frequencies and 200% of the frequency doubled frequencies.

31. The apparatus as claimed in claim 22 wherein the apparatus is configured to assess a condition causing impairment of the subject's visual fields including any one or more of glaucoma, age-related macular degeneration, diabetic retinopathy, stroke, and multiple sclerosis affecting one or both eyes of the subject.

32. The method as claimed in claim 20 wherein the visual impairment is localized to a part of the sensory fields.

* * * * *